United States Patent [19]
Dinsmore

[11] Patent Number: 5,885,995
[45] Date of Patent: Mar. 23, 1999

[54] INHIBITORS OF FARNESYL-PROTEIN TRANSFERASE

[75] Inventor: Christopher J. Dinsmore, Schwenksville, Pa.

[73] Assignee: Merck & Co., Inc., Rahway, N.J.

[21] Appl. No.: 827,482

[22] Filed: Mar. 27, 1997

Related U.S. Application Data

[60] Provisional application No. 60/014,792 Apr. 13, 1996.
[51] Int. Cl.$^6$ .................... A61K 31/495; C07D 401/00; C07D 403/00
[52] U.S. Cl. ..................... 514/252; 544/360; 544/370
[58] Field of Search ...................... 514/252, 218; 544/358, 370, 360; 540/575

[56] References Cited

U.S. PATENT DOCUMENTS

| | | | |
|---|---|---|---|
| 4,829,065 | 5/1989 | Pascal et al. | 514/255 |
| 4,940,793 | 7/1990 | Botre et al. | 544/349 |
| 5,478,934 | 12/1995 | Yuan et al. | 540/546 |
| 5,576,313 | 11/1996 | Fisher et al. | 514/211 |

FOREIGN PATENT DOCUMENTS

| | | |
|---|---|---|
| WO 96/30343 | 10/1996 | WIPO . |
| WO 96/31501 | 10/1996 | WIPO . |
| WO 96/37204 | 11/1996 | WIPO . |

OTHER PUBLICATIONS

Exp. Opin. Ther. Patents, vol. 5(12), pp. 1269–1271 (1995), by S. L. Graham.

Exp. Opin. Ther. Patents, vol. 6(12) (1996), pp. 1295–1304, by S. L. Graham, et al.

J. of Biol. Chem., vol. 268, No. 11, pp. 7617–7620 (1993), by J. B. Gibbs, et al.

J. of Biol. Chem., vol. 269, No. 44, pp. 27706–27714 (1994), by G. L. James, et al.

J. of Biol. Chem., vol. 270, No. 11, pp. 6221–6226 (1995), by G. L. James, et al.

Science, vol. 260, pp. 1934–1937 (1993), by N. E. Kohl, et al.

Proc. Natl. Acad. Sci. USA, vol. 91, pp. 9141–9145 (1994), by N. E. Kohl, et al.

Nature Medicine, vol. 1, No. 8, pp. 792–797 (1995), by N. E. Kohl, et al.

Cancer Research, vol. 55, pp. 5302–5309 (1995), by L. Sepp–Lorenzino, et al.

*Primary Examiner*—Amelia Owens
*Attorney, Agent, or Firm*—David A. Muthard; Mark R. Daniel

[57] ABSTRACT

The present invention is directed to compounds which inhibit farnesyl-protein transferase (FTase) and the farnesylation of the oncogene protein Ras. The invention is further directed to chemotherapeutic compositions containing the compounds of this invention and methods for inhibiting farnesyl-protein transferase and the farnesylation of the oncogene protein Ras.

12 Claims, No Drawings

INHIBITORS OF FARNESYL-PROTEIN TRANSFERASE

This application claims the benifit of provisional application Ser. No. 60/014792 filed Apr. 13, 1996.

BACKGROUND OF THE INVENTION

The Ras proteins (Ha-Ras, Ki4a-Ras, Ki4b-Ras and N-Ras) are part of a signalling pathway that links cell surface growth factor receptors to nuclear signals initiating cellular proliferation. Biological and biochemical studies of Ras action indicate that Ras functions like a G-regulatory protein. In the inactive state, Ras is bound to GDP. Upon growth factor receptor activation Ras is induced to exchange GDP for GTP and undergoes a conformational change. The GTP-bound form of Ras propagates the growth stimulatory signal until the signal is terminated by the intrinsic GTPase activity of Ras, which returns the protein to its inactive GDP bound form (D. R. Lowy and D. M. Willumsen, *Ann. Rev. Biochem.* 62:851–891 (1993)). Mutated ras genes (Ha-ras, Ki4a-ras, Ki4b-ras and N-ras) are found in many human cancers, including colorectal carcinoma, exocrine pancreatic carcinoma, and myeloid leukemias. The protein products of these genes are defective in their GTPase activity and constitutively transmit a growth stimulatory signal.

Ras must be localized to the plasma membrane for both normal and oncogenic functions. At least 3 post-translational modifications are involved with Ras membrane localization, and all 3 modifications occur at the C-terminus of Ras. The Ras C-terminus contains a sequence motif termed a "CAAX" or "Cys-Aaa$^1$-Aaa$^2$-Xaa" box (Cys is cysteine, Aaa is an aliphatic amino acid, the Xaa is any amino acid) (Willumsen et al., *Nature* 310:583–586 (1984)). Depending on the specific sequence, this motif serves as a signal sequence for the enzymes farnesyl-protein transferase or geranylgeranyl-protein transferase, which catalyze the alkylation of the cysteine residue of the CAAX motif with a $C_{15}$ or $C_{20}$ isoprenoid, respectively. (S. Clarke., *Ann. Rev. Biochem.* 61:355–386 (1992); W. R. Schafer and J. Rine, *Ann. Rev. Genetics* 30:209–237 (1992)). The Ras protein is one of several proteins that are known to undergo post-translational farnesylation. Other farnesylated proteins include the Ras-related GTP-binding proteins such as Rho, fungal mating factors, the nuclear lamins, and the gamma subunit of transducin. James, et al., *J. Biol. Chem.* 269, 14182 (1994) have identified a peroxisome associated protein Pxf which is also farnesylated. James, et al., have also suggested that there are farnesylated proteins of unknown structure and function in addition to those listed above.

Inhibition of farnesyl-protein transferase has been shown to block the growth of Ras-transformed cells in soft agar and to modify other aspects of their transformed phenotype. It has also been demonstrated that certain inhibitors of farnesyl-protein transferase selectively block the processing of the Ras oncoprotein intracellularly (N. E. Kohl et al., *Science*, 260:1934–1937 (1993) and G. L. James et al., *Science*, 260:1937–1942 (1993). Recently, it has been shown that an inhibitor of farnesyl-protein transferase blocks the growth of ras-dependent tumors in nude mice (N. E. Kohl et al., *Proc. Natl. Acad. Sci U.S.A.*, 91:9141–9145 (1994) and induces regression of mammary and salivary carcinomas in ras transgenic mice (N. E. Kohl et al., *Nature Medicine*, 1:792–797 (1995).

Indirect inhibition of farnesyl-protein transferase in vivo has been demonstrated with lovastatin (Merck & Co., Rahway, N.J.) and compactin (Hancock et al., ibid; Casey et al., ibid; Schafer et al., *Science* 245:379 (1989)). These drugs inhibit HMG-CoA reductase, the rate limiting enzyme for the production of polyisoprenoids including farnesyl pyrophosphate. Farnesyl-protein transferase utilizes farnesyl pyrophosphate to covalently modify the Cys thiol group of the Ras CAAX box with a farnesyl group (Reiss et al., *Cell*, 62:81–88 (1990); Schaber et al., *J. Biol Chem.*, 265:14701–14704 (1990); Schafer et al., *Science*, 249:1133–1139 (1990); Manne et al., *Proc. Natl. Acad. Sci USA*, 87:7541–7545 (1990)). Inhibition of farnesyl pyrophosphate biosynthesis by inhibiting HMG-CoA reductase blocks Ras membrane localization in cultured cells. However, direct inhibition of farnesyl-protein transferase would be more specific and attended by fewer side effects than would occur with the required dose of a general inhibitor of isoprene biosynthesis.

Inhibitors of farnesyl-protein transferase (FPTase) have been described in two general classes. The first are analogs of famesyl diphosphate (FPP), while the second class of inhibitors is related to the protein substrates (e.g., Ras) for the enzyme. The peptide derived inhibitors that have been described are generally cysteine containing molecules that are related to the CAAX motif that is the signal for protein prenylation. (Schaber et al., ibid; Reiss et. al., ibid; Reiss et al., *PNAS*, 88:732–736 (1991)). Such inhibitors may inhibit protein prenylation while serving as alternate substrates for the farnesyl-protein transferase enzyme, or may be purely competitive inhibitors (U.S. Pat. No. 5,141,851, University of Texas; N. E. Kohl et al., *Science*, 260:1934–1937 (1993); Graham, et al., *J. Med. Chem.*, 37,725 (1994)). In general, deletion of the thiol from a CAAX derivative has been shown to dramatically reduce the inhibitory potency of the compound. However, the thiol group potentially places limitations on the therapeutic application of FPTase inhibitors with respect to pharmacokinetics, pharmacodynamics and toxicity. Therefore, a functional replacement for the thiol is desirable.

It has recently been reported that famesyl-protein transferase inhibitors are inhibitors of proliferation of vascular smooth muscle cells and are therefore useful in the prevention and therapy of arteriosclerosis and diabetic disturbance of blood vessels (JP H7-112930).

It has recently been disclosed that certain tricyclic compounds which optionally incorporate a piperidine moiety are inhibitors of FPTase (WO 95/10514, WO 95/10515 and WO 95/10516). Imidazole-containing inhibitors of farnesyl protein transferase have also been disclosed (WO 95/09001 and EP 0 675 112 A1).

It is, therefore, an object of this invention to develop peptidomimetic compounds that do not have a thiol moiety, and that will inhibit farnesyl-protein transferase and thus, the post-translational farnesylation of proteins. It is a further object of this invention to develop chemotherapeutic compositions containing the compounds of this invention and methods for producing the compounds of this invention.

SUMMARY OF THE INVENTION

The present invention comprises peptidomimetic ketopiperazine-containing compounds which inhibit the farnesyl-protein transferase. The instant compounds lack a thiol moiety and thus offer unique advantages in terms of improved pharmacokinetic behavior in animals, prevention of thiol-dependent chemical reactions, such as rapid autoxidation and disulfide formation with endogenous thiols, and reduced systemic toxicity. Further contained in this invention are chemotherapeutic compositions containing these farnesyl transferase inhibitors and methods for their production.

The compounds of this invention are illustrated by the formulae A, B and C:

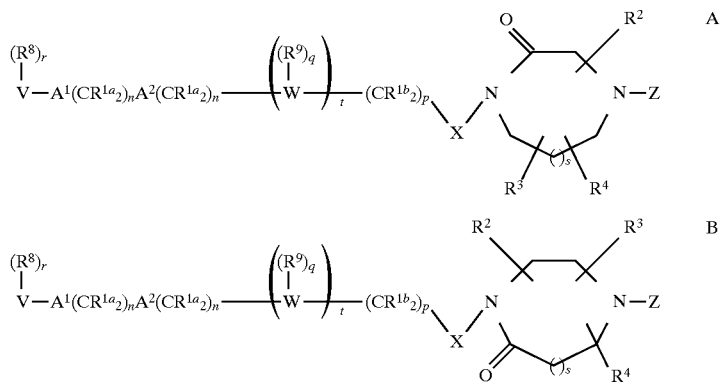

A

B

DETAILED DESCRIPTION OF THE INVENTION

The compounds of this invention are useful in the inhibition of farnesyl-protein transferase and the farnesylation of the oncogene protein Ras. In a first embodiment of this invention, the inhibitors of farnesyl-protein transferase are illustrated by the formula A:

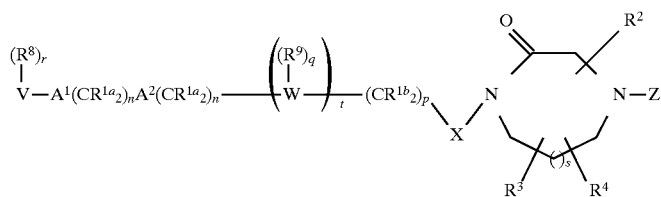

A wherein:
$R^{1a}$ and $R^{1b}$ are independently selected from:
a) hydrogen,
b) aryl, heterocycle, $C_3$–$C_{10}$ cycloalkyl, $C_2$–$C_6$ alkenyl, $C_2$–$C_6$ alkynyl, $R^{10}O$—, $R^{11}S(O)_m$—, $R^{10}C(O)NR^{10}$—, $(R^{10})_2NC(O)$—, $R^{10}{}_2N$—$C(NR^{10})$—, CN, $NO_2$, $R^{10}C(O)$—, $N_3$, —$N(R^{10})_2$, or $R^{11}OC(O)NR^{10}$—,
c) unsubstituted or substituted $C_1$–$C_6$ alkyl wherein the substitutent on the substituted $C_1$–$C_6$ alkyl is selected from unsubstituted or substituted aryl, heterocyclic, $C_3$–$C_{10}$ cycloalkyl, $C_2$–$C_6$ alkenyl, $C_2$–$C_6$ alkynyl, $R^{10}O$—, $R^{11}S(O)_m$—, $R^{10}C(O)NR^{10}$—, $(R^{10})_2NC(O)$—, $R^{10}{}_2N$—$C(NR^{10})$—, CN, $R^{10}C(O)$—, $N_3$, —$N(R^{10})_2$, and $R^{11}OC(O)$—$NR^{10}$—;

$R^2$ and $R^3$ are independently selected from: H; unsubstituted or substituted $C_{1-8}$ alkyl, unsubstituted or substituted $C_{2-8}$ alkenyl, unsubstituted or substituted $C_{2-8}$ alkynyl, unsubstituted or substituted aryl, unsubstituted or substituted heterocycle,

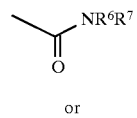

or

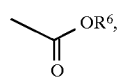

wherein the substituted group is substituted with one or more of:

1) aryl or heterocycle, unsubstituted or substituted with:
 a) $C_{1-4}$ alkyl,
 b) $(CH_2)_pOR^6$,
 c) $(CH_2)_pNR^6R^7$,
 d) halogen,
 e) CN,
 f) aryl or heteroaryl,
 g) perfluoro-$C_{1-4}$ alkyl,
 h) $SR^{6a}$, $S(O)R^{6a}$, $SO_2R^{6a}$,
2) $C_{3-6}$ cycloalkyl,
3) $OR^6$,
4) $SR^{6a}$, $S(O)R^{6a}$, or $SO_2R^{6a}$,
5) —$NR^6R^7$, 6) 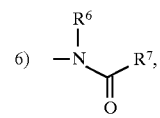

7) 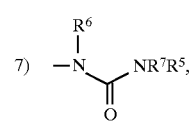

8) 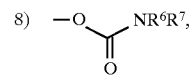

9) 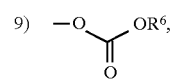

10) 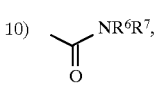

11) 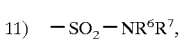

12) 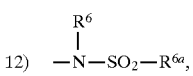

13) 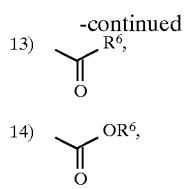

14) 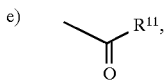

15) $N_3$,
16) F; or
17) perfluoro-$C_{1-4}$-alkyl, or $R^2$ and $R^3$ are attached to the same C atom and are combined to form —$(CH_2)_u$— wherein one of the carbon atoms is optionally replaced by a moiety selected from: O, $S(O)_m$, —NC(O)—, and —N($COR^{10}$)—;

$R^4$ is selected from H and $CH_3$;
and any two of $R^2$, $R^3$ and $R^4$ are optionally attached to the same carbon atom;

$R^5$, $R^6$ and $R^7$ are independently selected from: H; $C_{1-4}$ alkyl, $C_{3-6}$ cycloalkyl, heterocycle, aryl, aroyl, heteroaroyl, arylsulfonyl, heteroarylsulfonyl, unsubstituted or substituted with:
  a) $C_{1-4}$ alkoxy,
  b) aryl or heterocycle,
  c) halogen,
  d) HO, e) 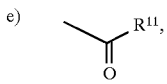

f) —$SO_2R^{11}$, or
  g) $N(R^{10})_2$; or $R^6$ and $R^7$ may be joined in a ring;
$R^7$ and $R^5$ may be joined in a ring;
$R^{6a}$ is selected from: $C_{1-4}$ alkyl, $C_{3-6}$ cycloalkyl, heterocycle, aryl, unsubstituted or substituted with:
  a) $C_{1-4}$ alkoxy,
  b) aryl or heterocycle,
  c) halogen,
  d) HO, e) 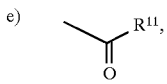

f) —$SO_2R^{11}$, or
  g) $N(R^{10})_2$;

$R^8$ is independently selected from:
  a) hydrogen,
  b) aryl, heterocycle, $C_3$–$C_{10}$ cycloalkyl, $C_2$–$C_6$ alkenyl, $C_2$–$C_6$ alkynyl, perfluoroalkyl, F, Cl, Br, $R^{10}O$—, $R^{11}S(O)_m$—, $R^{10}C(O)NR^{10}$—, $(R^{10})_2NC(O)$—, $R^{10}_2N$—$C(NR^{10})$—, CN, $NO_2$, $R^{10}C(O)$—, $N_3$, —$N(R^{10})_2$, or $R^{11}OC(O)NR^{10}$—, and
  c) $C_1$–$C_6$ alkyl unsubstituted or substituted by aryl, cyanophenyl, heterocycle, $C_3$–$C_{10}$ cycloalkyl, $C_2$–$C_6$ alkenyl, $C_2$–$C_6$ alkynyl, perfluoroalkyl, F, Cl, Br, $R^{10}O$—, $R^{11}S(O)_m$—, $R^{10}C(O)NH$—, $(R^{10})_2NC(O)$—, $R^{10}_2N$—$C(NR^{10})$—, CN, $R^{10}C(O)$—, $N_3$, —$N(R^{10})_2$, or $R^{10}OC(O)NH$—;

$R^9$ is selected from:
  a) hydrogen,
  b) alkenyl, alkynyl, perfluoroalkyl, F, Cl, Br, $R^{10}O$—, $R^{11}S(O)_m$—, $R^{10}C(O)NR^{10}$—, $(R^{10})_2NC(O)$—, $R^{10}_2N$—$C(NR^{10})$—, CN, $NO_2$, $R^{10}OC(O)$—, $N_3$, —$N(R^{10})_2$, or $R^{11}OC(O)NR^{10}$—, and
  c) $C_1$–$C_6$ alkyl unsubstituted or substituted by perfluoroalkyl, F, Cl, Br, $R^{10}O$—, $R^{11}S(O)_m$—, $R^{10}C(O)NR^{10}$—, $(R^{10})_2NC(O)$—, $R^{10}_2N$—$C(NR^{10})$—, CN, $R^{10}C(O)$—, $N_3$, —$N(R^{10})_2$, or $R^{11}OC(O)NR^{10}$—;

$R^{10}$ is independently selected from hydrogen, $C_1$–$C_6$ alkyl, benzyl and aryl;

$R^{11}$ is independently selected from $C_1$–$C_6$ alkyl and aryl;

$A^1$ and $A^2$ are independently selected from: a bond, —CH=CH—, —C≡C—, —C(O)—, —$C(O)NR^{10}$—, —$NR^{10}C(O)$—, O, —$N(R^{10})$—, —$S(O)_2N(R^{10})$—, —$N(R^{10})S(O)_2$—, or $S(O)_m$;

V is selected from:
  a) hydrogen,
  b) heterocycle,
  c) aryl,
  d) $C_1$–$C_{20}$ alkyl wherein from 0 to 4 carbon atoms are replaced with a a heteroatom selected from O, S, and N, and
  e) $C_2$–$C_{20}$ alkenyl,
provided that V is not hydrogen if $A^1$ is $S(O)_m$ and V is not hydrogen if $A^1$ is a bond, n is 0 and $A^2$ is $S(O)_m$;

W is a heterocycle;

X is a bond, —$CH_2$—, —C(=O)—, or —$S(=O)_m$—;

Z is selected from:
  1) a unsubstituted or substituted group selected from aryl, heteroaryl, arylmethyl, heteroarylmethyl, arylsulfonyl, heteroarylsulfonyl, wherein the substituted group is substituted with one or more of the following:
    a) $C_{1-4}$ alkyl, unsubstituted or substituted with:
       $C_{1-4}$ alkoxy, $NR^6R^7$, $C_{3-6}$ cycloalkyl, unsubstituted or substituted aryl, heterocycle, HO, —$S(O)_mR^{6a}$, or —$C(O)NR^6R^7$,
    b) aryl or heterocycle,
    c) halogen,
    d) $OR^6$,
    e) $NR^6R^7$,
    f) CN,
    g) $NO_2$,
    h) $CF_3$;
    i) —$S(O)_mR^{6a}$,
    j) —$C(O)NR^6R^7$, or
    k) $C_3$–$C_6$ cycloalkyl; or
  2) unsubstituted $C_1$–$C_6$ alkyl, substituted $C_1$–$C_6$ alkyl, unsubstituted $C_3$–$C_6$ cycloalkyl or substituted $C_3$–$C_6$ cycloalkyl, wherein the substituted $C_1$–$C_6$ alkyl and substituted $C_3$–$C_6$ cycloalkyl is substituted with one or two of the following:
    a) $C_{1-4}$ alkoxy,
    b) $NR^6R^7$,
    c) $C_{3-6}$ cycloalkyl,
    d) —$NR^6C(O)R^7$,
    e) HO,
    f) —$S(O)_mR^{6a}$,
    g) halogen, or
    h) perfluoroalkyl;

m is 0, 1 or 2;
n is 0, 1, 2, 3 or 4;
p is 0, 1, 2, 3 or 4;
q is 1 or 2;
r is 0 to 5, provided that r is 0 when V is hydrogen;
s is 0 or 1;

t is 0 or 1; and u is 4 or 5;

or the pharmaceutically acceptable salts thereof.

In a second embodiment of this invention, the inhibitors of farnesyl-protein transferase are illustrated by the formula B:

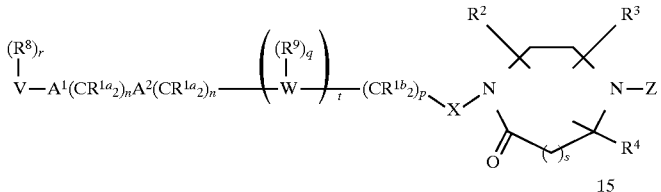

wherein:

$R^{1a}$ and $R^{1b}$ are independently selected from:
a) hydrogen,
b) aryl, heterocycle, $C_3$–$C_{10}$ cycloalkyl, $C_2$–$C_6$ alkenyl, $C_2$–$C_6$ alkynyl, $R^{10}O$—, $R^{11}S(O)_m$—, $R^{10}C(O)NR^{10}$—, $(R^{10})_2NC(O)$—, $R^{10}{}_2N$—$C(NR^{10})$—, CN, $NO_2$, $R^{10}C(O)$—, $N_3$, —$N(R^{10})_2$, or $R^{11}OC(O)NR^{10}$—,
c) unsubstituted or substituted $C_1$–$C_6$ alkyl wherein the substitutent on the substituted $C_1$–$C_6$ alkyl is selected from unsubstituted or substituted aryl, heterocyclic, $C_3$–$C_{10}$ cycloalkyl, $C_2$–$C_6$ alkenyl, $C_2$–$C_6$ alkynyl, $R^{10}O$—, $R^{11}S(O)_m$—, $R^{10}C(O)NR^{10}$—, $(R^{10})_2NC(O)$—, $R^{10}{}_2N$—$C(NR^{10})$—, CN, $R^{10}C(O)$—, $N_3$, —$N(R^{10})_2$, and $R^{11}OC(O)$—$NR^{10}$—;

$R^2$ and $R^3$ are independently selected from: H; unsubstituted or substituted $C_{1-8}$ alkyl, unsubstituted or substituted $C_{2-8}$ alkenyl, unsubstituted or substituted $C_{2-8}$ alkynyl, unsubstituted or substituted aryl, unsubstituted or substituted heterocycle,

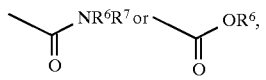

wherein the substituted group is substituted with one or more of:
1) aryl or heterocycle, unsubstituted or substituted with:
   a) $C_{1-4}$ alkyl,
   b) $(CH_2)_pOR^6$,
   c) $(CH_2)_pNR^6R^7$,
   d) halogen,
   e) CN,
   f) aryl or heteroaryl,
   g) perfluoro-$C_{1-4}$ alkyl,
   h) $SR^{6a}$, $S(O)R^{6a}$, $SO_2R^{6a}$,
2) $C_{3-6}$ cycloalkyl,
3) $OR^6$,
4) $SR^{6a}$, $S(O)R^{6a}$, or $SO_2R^{6a}$,
5) —$NR^6R^7$,

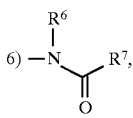

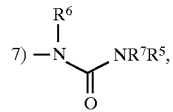

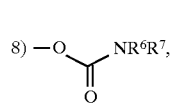

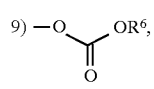

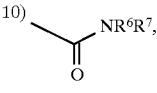

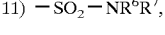

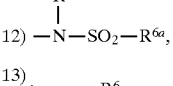

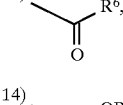

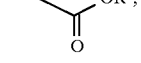

15) $N_3$,
16) F; or
17) perfluoro-$C_{1-4}$-alkyl, or $R^2$ and $R^3$ are attached to the same C atom and are combined to form —$(CH_2)_u$— wherein one of the carbon atoms is optionally replaced by a moiety selected from: O, $S(O)_m$, —NC(O)—, and —$N(COR^{10})$—;

$R^4$ is selected from H and $CH_3$;

and any two of $R^2$, $R^3$ and $R^4$ are optionally attached to the same carbon atom;

$R^5$, $R^6$ and $R^7$ are independently selected from: H; $C_{1-4}$ alkyl, $C_{3-6}$ cycloalkyl, heterocycle, aryl, aroyl, heteroaroyl, arylsulfonyl, heteroarylsulfonyl, unsubstituted or substituted with:
a) $C_{1-4}$ alkoxy,
b) aryl or heterocycle,
c) halogen,
d) HO,

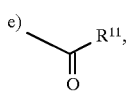

f) —$SO_2R^{11}$, or
g) $N(R^{10})_2$; or $R^6$ and $R^7$ may be joined in a ring;

$R^7$ and $R^{7a}$ may be joined in a ring;

$R^{6a}$ is selected from: $C_{1-4}$ alkyl, $C_{3-6}$ cycloalkyl, heterocycle, aryl, unsubstituted or substituted with:
  a) $C_{1-4}$ alkoxy,
  b) aryl or heterocycle,
  c) halogen,
  d) HO,
  e) $\overset{O}{\underset{\|}{C}}\!\!-\!R^{11}$,
  f) $-SO_2R^{11}$, or
  g) $N(R^{10})_2$;

$R^8$ is independently selected from:
  a) hydrogen,
  b) aryl, heterocycle, $C_3$–$C_{10}$ cycloalkyl, $C_2$–$C_6$ alkenyl, $C_2$–$C_6$ alkynyl, perfluoroalkyl, F, Cl, Br, $R^{10}O-$, $R^{11}S(O)_m-$, $R^{10}C(O)NR^{10}-$, $(R^{10})_2NC(O)-$, $R^{10}{}_2N-C(NR^{10})-$, CN, $NO_2$, $R^{10}C(O)-$, $N_3$, $-N(R^{10})_2$, or $R^{11}OC(O)NR^{10}-$, and
  c) $C_1$–$C_6$ alkyl unsubstituted or substituted by aryl, cyanophenyl, heterocycle, $C_3$–$C_{10}$ cycloalkyl, $C_2$–$C_6$ alkenyl, $C_2$–$C_6$ alkynyl, perfluoroalkyl, F, Cl, Br, $R^{10}O-$, $R^{11}S(O)_m-$, $R^{10}C(O)NH-$, $(R^{10})_2NC(O)-$, $R^{10}{}_2N-C(NR^{10})-$, CN, $R^{10}C(O)-$, $N_3$, $-N(R^{10})_2$, or $R^{10}OC(O)NH-$;

$R^9$ is selected from:
  a) hydrogen,
  b) $C_2$–$C_6$ alkenyl, $C_2$–$C_6$ alkynyl, perfluoroalkyl, F, Cl, Br, $R^{10}O-$, $R^{11}S(O)_m-$, $R^{10}C(O)NR^{10}-$, $(R^{10})_2NC(O)-$, $R^{10}{}_2N-C(NR^{10})-$, CN, $NO_2$, $R^{10}C(O)-$, $N_3$, $-N(R^{10})_2$, or $R^{11}OC(O)NR^{10}-$, and
  c) $C_1$–$C_6$ alkyl unsubstituted or substituted by perfluoroalkyl, F, Cl, Br, $R^{10}O-$, $R^{11}S(O)_m-$, $R^{10}C(O)NR^{10}-$, $(R^{10})_2NC(O)-$, $R^{10}{}_2N-C(NR^{10})-$, CN, $R^{10}C(O)-$, $N_3$, $-N(R^{10})_2$, or $R^{11}OC(O)NR^{10}-$;

$R^{10}$ is independently selected from hydrogen, $C_1$–$C_6$ alkyl, benzyl and aryl;

$R^{11}$ is independently selected from $C_1$–$C_6$ alkyl and aryl;

$A^1$ and $A^2$ are independently selected from: a bond, $-CH=CH-$, $-C\equiv C-$, $-C(O)-$, $-C(O)NR^{10}-$, $-NR^{10}C(O)-$, O, $-N(R^{10})-$, $-S(O)_2N(R^{10})-$, $-N(R^{10})S(O)_2-$, or $S(O)_m$;

V is selected from:
  a) hydrogen,
  b) heterocycle,
  c) aryl,
  d) $C_1$–$C_{20}$ alkyl wherein from 0 to 4 carbon atoms are replaced with a a heteroatom selected from O, S, and N, and
  e) $C_2$–$C_{20}$ alkenyl, provided that V is not hydrogen if $A^1$ is $S(O)_m$ and V is not hydrogen if $A^1$ is a bond, n is 0 and $A^2$ is $S(O)_m$;

W is a heterocycle;

X is a bond, $-CH_2-$, $-C(=O)-$, or $-S(=O)_m-$;

Z is selected from:
  1) a unsubstituted or substituted group selected from aryl, heteroaryl, arylmethyl, heteroarylmethyl, arylsulfonyl, heteroarylsulfonyl, wherein the substituted group is substituted with one or more of the following:
    a) $C_{1-4}$ alkyl, unsubstituted or substituted with:
      $C_{1-4}$ alkoxy, $NR^6R^7$, $C_{3-6}$ cycloalkyl, unsubstituted or substituted aryl, heterocycle, HO, $-S(O)_mR^{6a}$, or $-C(O)NR^6R^7$,
    b) aryl or heterocycle,
    c) halogen,
    d) $OR^6$,
    e) $NR^6R^7$,
    f) CN,
    g) $NO_2$,
    h) $CF_3$;
    i) $-S(O)_mR^{6a}$,
    j) $-C(O)NR^6R^7$, or
    k) $C_3$–$C_6$ cycloalkyl; or
  2) unsubstituted $C_1$–$C_6$ alkyl, substituted $C_1$–$C_6$ alkyl, unsubstituted $C_3$–$C_6$ cycloalkyl or substituted $C_3$–$C_6$ cycloalkyl, wherein the substituted $C_1$–$C_6$ alkyl and substituted $C_3$–$C_6$ cycloalkyl is substituted with one or two of the following:
    a) $C_{1-4}$ alkoxy,
    b) $NR^6R^7$,
    c) $C_{3-6}$ cycloalkyl,
    d) $-NR^6C(O)R^7$,
    e) HO,
    f) $-S(O)_mR^{6a}$,
    g) halogen, or
    h) perfluoroalkyl;

m is 0, 1 or 2;

n is 0, 1, 2, 3 or 4;

p is 0, 1, 2, 3 or 4;

q is 1 or 2;

r is 0 to 5, provided that r is 0 when V is hydrogen;

s is 1;

t is 0 or 1; and u is 4 or 5;

or the pharmaceutically acceptable salts thereof.

A preferred embodiment of the compounds of this invention is illustrated by the following formula:

$$V-A^1(CR^{1a}{}_2)_nA^2(CR^{1a}{}_2)_n-\overset{(R^8)_r}{|}\left(\overset{(R^9)_q}{\underset{|}{W}}\right)_t-(CR^{1b}{}_2)_p-\overset{X}{\underset{R^3\ R^4}{\diagdown N\diagup}}\overset{O\quad R^2\ A}{\underset{}{\diagdown\diagup\diagdown}}N-Z$$

wherein:

$R^{1a}$ is independently selected from: hydrogen or $C_1$–$C_6$ alkyl;

$R^{1b}$ is independently selected from:
  a) hydrogen,
  b) aryl, heterocycle, cycloalkyl, $R^{10}O-$, $-N(R^{10})_2$ or $C_2$–$C_6$ alkenyl, c) unsubstituted or substituted $C_1-C_6$ alkyl wherein the substitutent on the substituted $C_1-C_6$ alkyl is selected from unsubstituted or substituted aryl, heterocycle, cycloalkyl, alkenyl, $R^{10}O$— and —$N(R^{10})_2$;

$R^3$ and $R^4$ are independently selected from H and $CH_3$;

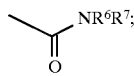

$R^2$ is H;

or $C_{1-5}$ alkyl, unbranched or branched, unsubstituted or substituted with one or more of:
1) aryl,
2) heterocycle,
3) $OR^6$,
4) $SR^{6a}$, $SO_2R^{6a}$, or 5) 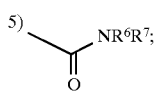

and any two of $R^2$, $R^3$, $R^4$, and $R^5$ are optionally attached to the same carbon atom;

$R^6$ and $R^7$ are independently selected from:
H; $C_{1-4}$ alkyl, $C_{3-6}$ cycloalkyl, aryl, heterocycle, unsubstituted or substituted with:
a) $C_{1-4}$ alkoxy,
b) halogen, or
c) aryl or heterocycle;

$R^{6a}$ is selected from:
$C_{1-4}$ alkyl or $C_{3-6}$ cycloalkyl, unsubstituted or substituted with:
a) $C_{1-4}$ alkoxy,
b) halogen, or
c) aryl or heterocycle;

$R^8$ is independently selected from:
a) hydrogen,
b) $C_1-C_6$ alkyl, $C_2-C_6$ alkenyl, $C_2-C_6$ alkynyl, $C_1-C_6$ perfluoroalkyl, F, Cl, $R^{10}O$—, $R^{10}C(O)NR^{10}$—, CN, $NO_2$, $(R^{10})_2N$—$C(NR^{10})$—, $R^{10}C(O)$—, —$N(R^{10})_2$, or $R^{11}OC(O)NR^{10}$—, and
c) $C_1-C_6$ alkyl substituted by $C_1-C_6$ perfluoroalkyl, $R^{10}O$—, $R^{10}C(O)NR^{10}$—, $(R^{10})_2N$—$C(NR^{10})$—, $R^{10}C(O)$—, —$N(R^{10})_2$, or $R^{11}OC(O)NR^{10}$—;

$R^9$ is selected from:
a) hydrogen,
b) $C_2-C_6$ alkenyl, $C_2-C_6$ alkynyl, $C_1-C_6$ perfluoroalkyl, F, Cl, $R^{10}O$—, $R^{11}S(O)_m$—, $R^{10}C(O)NR^{10}$—, CN, $NO_2$, $(R^{10})_2N$—$C(NR^{10})$—, $R^{10}C(O)$—, —$N(R^{10})_2$, or $R^{11}OC(O)NR^{10}$—, and
c) $C_1-C_6$ alkyl unsubstituted or substituted by $C_1-C_6$ perfluoroalkyl, F, Cl, $R^{10}O$—, $R^{11}S(O)_m$—, $R^{10}C(O)NR^{10}$—, CN, $(R^{10})_2N$—$C(NR^{10})$—, $R^{10}C(O)$—, —$N(R^{10})_2$, or $R^{11}OC(O)NR^{10}$—;

$R^{10}$ is independently selected from hydrogen, $C_1-C_6$ alkyl, benzyl and aryl;

$R^{11}$ is independently selected from $C_1-C_6$ alkyl and aryl;

$A^1$ and $A^2$ are independently selected from: a bond, —CH=CH—, —C≡C—, —C(O)—, —C(O)NR^{10}—, O, —N(R^{10})—, or $S(O)_m$;

V is selected from:
a) hydrogen,
b) heterocycle selected from pyrrolidinyl, imidazolyl, pyridinyl, thiazolyl, pyridonyl, 2-oxopiperidinyl, indolyl, quinolinyl, isoquinolinyl, and thienyl,
c) aryl,
d) $C_1-C_{20}$ alkyl wherein from 0 to 4 carbon atoms are replaced with a a heteroatom selected from O, S, and N, and
e) $C_2-C_{20}$ alkenyl, and provided that V is not hydrogen if $A^1$ is $S(O)_m$ and V is not hydrogen if $A^1$ is a bond, n is 0 and $A^2$ is $S(O)_m$;

W is a heterocycle selected from pyrrolidinyl, imidazolyl, pyridinyl, thiazolyl, pyridonyl, 2-oxopiperidinyl, indolyl, quinolinyl, or isoquinolinyl;

X is —$CH_2$— or —C(=O)—;

Z is selected from:
1) a unsubstituted or substituted group selected from aryl, heteroaryl, arylmethyl, heteroarylmethyl, arylsulfonyl, heteroarylsulfonyl, wherein the substituted group is substituted with one or more of the following:
a) $C_{1-4}$ alkyl, unsubstituted or substituted with:
$C_{1-4}$ alkoxy, $NR^6R^7$, $C_{3-6}$ cycloalkyl, unsubstituted or substituted aryl, heterocycle, HO, —$S(O)_mR^{6a}$, or —$C(O)NR^6R^7$,
b) aryl or heterocycle,
c) halogen,
d) $OR^6$,
e) $NR^6R^7$,
f) CN,
g) $NO_2$,
h) $CF_3$;
i) —$S(O)_mR^{6a}$,
j) —$C(O)NR^6R^7$, or
k) $C_3-C_6$ cycloalkyl; or
2) unsubstituted $C_1-C_6$ alkyl, substituted $C_1-C_6$ alkyl, unsubstituted $C_3-C_6$ cycloalkyl or substituted $C_3-C_6$ cycloalkyl, wherein the substituted $C_1-C_6$ alkyl and substituted $C_3-C_6$ cycloalkyl is substituted with one or two of the following:
a) $C_{1-4}$ alkoxy,
b) $NR^6R^7$,
c) $C_{3-6}$ cycloalkyl,
d) —$NR^6C(O)R^7$,
e) HO,
f) —$S(O)_mR^{6a}$,
g) halogen, or
h) perfluoroalkyl;

m is 0, 1 or 2;

n is 0, 1, 2, 3 or 4;

p is 0, 1, 2, 3 or 4;

r is 0 to 5, provided that r is 0 when V is hydrogen;

s is 0 or 1;

t is 0 or 1; and u is 4 or 5;

provided that when X is —C(=O)—, or —S(=O)_m—, then t is 1 and the substitutent $(R^8)_r$— V—$A^1(CR^{1a}_2)_n$ $A^2(CR^{1a}_2)_n$— is not H;

or the pharmaceutically acceptable salts thereof.

A preferred embodiment of the compounds of this invention are illustrated by the formula C:

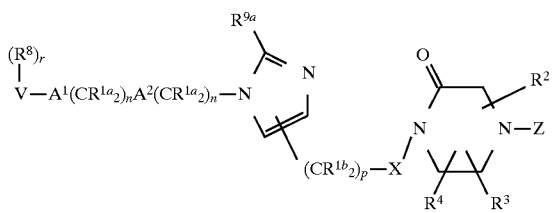

C wherein:

$R^{1a}$ is selected from: hydrogen or $C_1-C_6$ alkyl;

$R^{1b}$ is independently selected from:
  a) hydrogen,
  b) aryl, heterocycle, cycloalkyl, $R^{10}O-$, $-N(R^{10})_2$ or $C_2-C_6$ alkenyl,
  c) $C_1-C_6$ alkyl unsubstituted or substituted by aryl, heterocycle, cycloalkyl, alkenyl, $R^{10}O-$, or $-N(R^{10})_2$;

$R^3$ is selected from H and $CH_3$;

$R^2$ is selected from H;

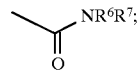

or $C_{1-5}$ alkyl, unbranched or branched, unsubstituted or substituted with one or more of:
  1) aryl,
  2) heterocycle,
  3) $OR^6$,
  4) $SR^{6a}$, $SO_2R^{6a}$, or

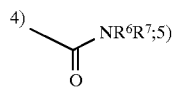

and $R^2$ and $R^3$ are optionally attached to the same carbon atom;

$R^6$ and $R^7$ are independently selected from:
  H; $C_{1-4}$ alkyl, $C_{3-6}$ cycloalkyl, aryl, heterocycle, unsubstituted or substituted with:
    a) $C_{1-4}$ alkoxy,
    b) halogen, or
    c) aryl or heterocycle;

$R^{6a}$ is selected from:
  $C_{1-4}$ alkyl or $C_{3-6}$ cycloalkyl, unsubstituted or substituted with:
    a) $C_{1-4}$ alkoxy,
    b) halogen, or
    c) aryl or heterocycle;

$R^8$ is independently selected from:
  a) hydrogen,
  b) $C_1-C_6$ alkyl, $C_2-C_6$ alkenyl, $C_2-C_6$ alkynyl, $C_1-C_6$ perfluoroalkyl, F, Cl, $R^{10}O-$, $R^{10}C(O)NR^{10}-$, CN, $NO_2$, $(R^{10})_2N-C(NR^{10})-$, $R^{10}C(O)-$, $-N(R^{10})_2$, or $R^{11}OC(O)NR^{10}-$, and
  c) $C_1-C_6$ alkyl substituted by $C_1-C_6$ perfluoroalkyl, $R^{10}O-$, $R^{10}C(O)NR^{10}-$, $(R^{10})_2N-C(NR^{10})-$, $R^{10}C(O)-$, $-N(R^{10})_2$, or $R^{11}OC(O)NR^{10}-$;

$R^{9a}$ is hydrogen or methyl;

$R^{10}$ is independently selected from hydrogen, $C_1-C_6$ alkyl, benzyl and aryl;

$R^{11}$ is independently selected from $C_1-C_6$ alkyl and aryl;

$A^1$ and $A^2$ are independently selected from: a bond, $-CH=CH-$, $-C\equiv C-$, $-C(O)-$, $-C(O)NR^{10}-$, $O$, $-N(R^{10})-$, or $S(O)_m$;

V is selected from:
  a) hydrogen,
  b) heterocycle selected from pyrrolidinyl, imidazolyl, pyridinyl, thiazolyl, pyridonyl, 2-oxopiperidinyl, indolyl, quinolinyl, isoquinolinyl, and thienyl,
  c) aryl,
  d) $C_1-C_{20}$ alkyl wherein from 0 to 4 carbon atoms are replaced with a a heteroatom selected from O, S, and N, and
  e) $C_2-C_{20}$ alkenyl, and
provided that V is not hydrogen if $A^1$ is $S(O)_m$ and V is not hydrogen if $A^1$ is a bond, n is 0 and $A^2$ is $S(O)_m$;

X is $-CH_2-$ or $-C(=O)-$;

Z is selected from:
  1) a unsubstituted or substituted group selected from aryl, heteroaryl, arylmethyl, heteroarylmethyl, arylsulfonyl, heteroarylsulfonyl, wherein the substituted group is substituted with one or more of the following:
    a) $C_{1-4}$ alkyl, unsubstituted or substituted with:
      $C_{1-4}$ alkoxy, $NR^6R^7$, $C_{3-6}$ cycloalkyl, unsubstituted or substituted aryl, heterocycle, HO, $-S(O)_mR^{6a}$, or $-C(O)NR^6R^7$,
    b) aryl or heterocycle,
    c) halogen,
    d) $OR^6$,
    e) $NR^6R^7$,
    f) CN,
    g) $NO_2$,
    h) $CF_3$;
    i) $-S(O)_mR^{6a}$,
    j) $-C(O)NR^6R^7$, or
    k) $C_3-C_6$ cycloalkyl; or
  2) unsubstituted $C_1-C_6$ alkyl, substituted $C_1-C_6$ alkyl, unsubstituted $C_3-C_6$ cycloalkyl or substituted $C_3-C_6$ cycloalkyl, wherein the substituted $C_1-C_6$ alkyl and substituted $C_3-C_6$ cycloalkyl is substituted with one or two of the following:
    a) $C_{1-4}$ alkoxy,
    b) $NR^6R^7$,
    c) $C_{3-6}$ cycloalkyl,
    d) $-NR^6C(O)R^7$,
    e) HO,
    f) $-S(O)_mR^{6a}$,
    g) halogen, or
    h) perfluoroalkyl;

m is 0, 1 or 2;

n is 0, 1, 2, 3 or 4;

p is 0, 1, 2, 3 or 4; and r is 0 to 5, provided that r is 0 when V is hydrogen;

provided that when X is $-C(=O)-$, or $-S(=O)_m-$, then t is 1 and the substitutent $(R^8)_r-V-A^1(CR^{1a}_2)_n A^2(CR^{1a}_2)_n-$ is not H;

or the pharmaceutically acceptable salts thereof.

In a more preferred embodiment of this invention, the inhibitors of farnesyl-protein transferase are illustrated by the formula D:

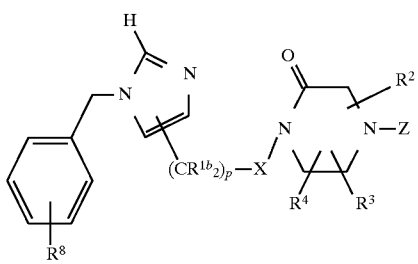

wherein:

$R^{1b}$ is independently selected from:
  a) hydrogen,
  b) aryl, heterocycle, cycloalkyl, $R^{10}O-$, $-N(R^{10})_2$ or $C_2$–$C_6$ alkenyl,
  c) $C_1$–$C_6$ alkyl unsubstituted or substituted by aryl, heterocycle, cycloalkyl, alkenyl, $R^{10}O-$, or $-N(R^{10})_2$;

$R^3$ is selected from H and $CH_3$;

$R^2$ is selected from H;

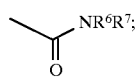

or $C_{1-5}$ alkyl, unbranched or branched, unsubstituted or substituted with one or more of:
  1) aryl,
  2) heterocycle,
  3) $OR^6$,
  4) $SR^{6a}$, $SO_2R^{6a}$, or

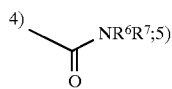

and $R^2$ and $R^3$ are optionally attached to the same carbon atom;

$R^6$ and $R^7$ are independently selected from:
  H; $C_{1-4}$ alkyl, $C_{3-6}$ cycloalkyl, aryl, heterocycle, unsubstituted or substituted with:
    a) $C_{1-4}$ alkoxy,
    b) halogen, or
    c) aryl or heterocycle;

$R^{6a}$ is selected from:
  $C_{1-4}$ alkyl or $C_{3-6}$ cycloalkyl, unsubstituted or substituted with:
    a) $C_{1-4}$ alkoxy,
    b) halogen, or
    c) aryl or heterocycle;

$R^8$ is independently selected from:
  a) hydrogen,
  b) $C_1$–$C_6$ alkyl, $C_2$–$C_6$ alkenyl, $C_2$–$C_6$ alkynyl, $C_1$–$C_6$ perfluoroalkyl, F, Cl, $R^{10}O-$, $R^{10}C(O)NR^{10}-$, CN, $NO_2$, $(R^{10})_2N-C(NR^{10})-$, $R^{10}C(O)-$, $-N(R^{10})_2$, or $R^{11}OC(O)NR^{10}-$, and
  c) $C_1$–$C_6$ alkyl substituted by $C_1$–$C_6$ perfluoroalkyl, $R^{10}O-$, $R^{10}C(O)NR^{10}-$, $(R^{10})_2N-C(NR^{10})-$, $R^{10}C(O)-$, $-N(R^{10})_2$, or $R^{11}OC(O)NR^{10}-$;

$R^{10}$ is independently selected from hydrogen, $C_1$–$C_6$ alkyl, benzyl and aryl;

$R^{11}$ is independently selected from $C_1$–$C_6$ alkyl and aryl;

X is $-CH_2-$ or $-C(=O)-$;

Z is selected from:
  1) a unsubstituted or substituted group selected from aryl, heteroaryl, arylmethyl, heteroarylmethyl, arylsulfonyl, heteroarylsulfonyl, wherein the substituted group is substituted with one or more of the following:
    a) $C_{1-4}$ alkyl, unsubstituted or substituted with:
      $C_{1-4}$ alkoxy, $NR^6R^7$, $C_{3-6}$ cycloalkyl, unsubstituted or substituted aryl, heterocycle, HO, $-S(O)_mR^{6a}$, or $-C(O)NR^6R^7$,
    b) aryl or heterocycle,
    c) halogen,
    d) $OR^6$,
    e) $NR^6R^7$,
    f) CN,
    g) $NO_2$,
    h) $CF_3$;
    i) $-S(O)_mR^{6a}$,
    j) $-C(O)NR^6R^7$, or
    k) $C_3$–$C_6$ cycloalkyl; or
  2) unsubstituted $C_1$–$C_6$ alkyl, substituted $C_1$–$C_6$ alkyl, unsubstituted $C_3$–$C_6$ cycloalkyl or substituted $C_3$–$C_6$ cycloalkyl, wherein the substituted $C_1$–$C_6$ alkyl and substituted $C_3$–$C_6$ cycloalkyl is substituted with one or two of the following:
    a) $C_{1-4}$ alkoxy,
    b) $NR^6R^7$,
    c) $C_{3-6}$ cycloalkyl,
    d) $-NR^6C(O)R^7$,
    e) HO,
    f) $-S(O)_mR^{6a}$,
    g) halogen, or
    h) perfluoroalkyl;

m is 0, 1 or 2; and p is 0, 1, 2, 3 or 4;

or the pharmaceutically acceptable salts thereof.

The preferred compounds of this invention are as follows:
4-(3-Chlorophenyl)-1-[1-(4-cyanobenzyl)-5-imidazolylmethyl]-2-piperazinone
(S)-6-n-Butyl-1-[1-(4-cyanobenzyl)-5-imidazolylmethyl]-4-(2,3-dimethylphenyl)-2-piperazinone and
4-(3-Chlorophenyl)-1-[(3-(4-cyanobenzyl)pyridin-4-yl)methyl]-2-piperazinone
or the pharmaceutically acceptable salt or optical isomer thereof.

Specific examples of the compounds of the invention are:
4-(3-Chlorophenyl)-1-[1-(4-cyanobenzyl)-5-imidazolylmethyl]-2-piperazinone

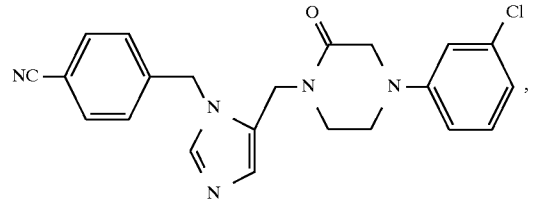

or the pharmaceutically acceptable salts thereof.

The compounds of the present invention may have asymmetric centers and occur as racemates, racemic mixtures, and as individual diastereomers, with all possible isomers, including optical isomers, being included in the present invention. When any variable (e.g. aryl, heterocycle, $R^1$, $R^2$ etc.) occurs more than one time in any constituent, its definition on each occurence is independent at every other occurence. Also, combinations of substituents/or variables are permissible only if such combinations result in stable compounds.

As used herein, "alkyl" is intended to include both branched and straight-chain saturated aliphatic hydrocarbon groups having the specified number of carbon atoms; "alkoxy" represents an alkyl group of indicated number of carbon atoms attached through an oxygen bridge. "Halogen" or "halo" as used herein means fluoro, chloro, bromo and iodo.

As used herein, "aryl" is intended to mean any stable monocyclic or bicyclic carbon ring of up to 7 members in each ring, wherein at least one ring is aromatic. Examples of such aryl elements include phenyl, naphthyl, tetrahydronaphthyl, indanyl, biphenyl, phenanthryl, anthryl or acenaphthyl.

The term heterocycle or heterocyclic, as used herein, represents a stable 5- to 7-membered monocyclic or stable 8- to 11-membered bicyclic heterocyclic ring which is either saturated or unsaturated, and which consists of carbon atoms and from one to four heteroatoms selected from the group consisting of N, O, and S, and including any bicyclic group in which any of the above-defined heterocyclic rings is fused to a benzene ring. The heterocyclic ring may be attached at any heteroatom or carbon atom which results in the creation of a stable structure. Examples of such heterocyclic elements include, but are not limited to, azepinyl, benzimidazolyl, benzisoxazolyl, benzofurazanyl, benzopyranyl, benzothiopyranyl, benzofuryl, benzothiazolyl, benzothienyl, benzoxazolyl, chromanyl, cinnolinyl, dihydrobenzofuryl, dihydrobenzothienyl, dihydrobenzothiopyranyl, dihydrobenzothiopyranyl sulfone, furyl, imidazolidinyl, imidazolinyl, imidazolyl, indolinyl, indolyl, isochromanyl, isoindolinyl, isoquinolinyl, isothiazolidinyl, isothiazolyl, isothiazolidinyl, morpholinyl, naphthyridinyl, oxadiazolyl, 2-oxoazepinyl, oxazolyl, 2-oxopiperazinyl, 2-oxopiperdinyl, 2-oxopyrrolidinyl, piperidyl, piperazinyl, pyridyl, pyrazinyl, pyrazolidinyl, pyrazolyl, pyridazinyl, pyrimidinyl, pyrrolidinyl, pyrrolyl, quinazolinyl, quinolinyl, quinoxalinyl, tetrahydrofuryl, tetrahydroisoquinolinyl, tetrahydroquinolinyl, thiamorpholinyl, thiamorpholinyl sulfoxide, thiazolyl, thiazolinyl, thienofuryl, thienothienyl, and thienyl.

As used herein, "heteroaryl" is intended to mean any stable monocyclic or bicyclic carbon ring of up to 7 members in each ring, wherein at least one ring is aromatic and wherein from one to four carbon atoms are replaced by heteroatoms selected from the group consisting of N, O, and S. Examples of such heterocyclic elements include, but are not limited to, benzimidazolyl, benzisoxazolyl, benzofurazanyl, benzopyranyl, benzothiopyranyl, benzofuryl, benzothiazolyl, benzothienyl, benzoxazolyl, chromanyl, cinnolinyl, dihydrobenzofuryl, dihydrobenzothienyl, dihydrobenzothiopyranyl, dihydrobenzothiopyranyl sulfone, furyl, imidazolyl, indolinyl, indolyl, isochromanyl, isoindolinyl, isoquinolinyl, isothiazolyl, naphthyridinyl, oxadiazolyl, pyridyl, pyrazinyl, pyrazolyl, pyridazinyl, pyrimidinyl, pyrrolyl, quinazolinyl, quinolinyl, quinoxalinyl, tetrahydroisoquinolinyl, tetrahydroquinolinyl, thiazolyl, thienofuryl, thienothienyl, and thienyl.

As used herein in the definition of $R^2$ and $R^3$, the term "the substituted group" intended to mean a substituted $C_{1-8}$ alkyl, substituted $C_{2-8}$ alkenyl, substituted $C_{2-8}$ alkynyl, substituted aryl or substituted heterocycle from which the substitutent(s) $R^2$ and $R^3$ are selected.

As used herein in the definition of $R^6$, $R^{6a}$, $R^7$ and $R^{7a}$, the substituted $C_{1-8}$ alkyl, substituted $C_{3-6}$ cycloalkyl, substituted aroyl, substituted aryl, substituted heteroaroyl, substituted arylsulfonyl, substituted heteroarylsulfonyl and substituted heterocycle include moieties containing from 1 to 3 substitutents in addition to the point of attachment to the rest of the compound.

As used herein, the terms "substituted aryl", "substituted heterocycle" and "substituted cycloalkyl" are intended to include the cyclic group which is substituted with 1 or 2 substitutents selected from the group which includes but is not limited to F, Cl, Br, $CF_3$, $NH_2$, $N(C_1-C_6 \text{ alkyl})_2$, $NO_2$, CN, $(C_1-C_6 \text{ alkyl})O$—, —OH, $(C_1-C_6 \text{ alkyl})S(O)_m$—, $(C_1-C_6 \text{ alkyl})C(O)NH$—, $H_2N$—C(NH)—, $(C_1-C_6 \text{ alkyl})C(O)$—, $(C_1-C_6 \text{ alkyl})OC(O)$—, $N_3$, $(C_1-C_6 \text{ alkyl})OC(O)NH$— and $C_1-C_{20}$ alkyl.

When $R^2$ and $R^3$ are combined to form—$(CH_2)_u$—, cyclic moieties are formed. Examples of such cyclic moieties include, but are not limited to:

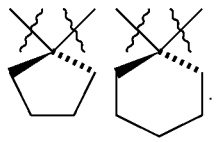

In addition, such cyclic moieties may optionally include a heteroatom(s). Examples of such heteroatom-containing cyclic moieties include, but are not limited to:

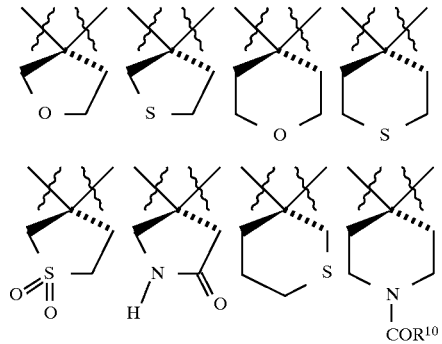

Lines drawn into the ring systems from substituents (such as from $R^2$, $R^3$, $R^4$ etc.) indicate that the indicated bond may be attached to any of the substitutable ring carbon atoms.

Preferably, $R^{1a}$ and $R^{1b}$ are independently selected from: hydrogen, —$N(R^{10})_2$, $R^{10}C(O)NR^{10}$— or unsubstituted or substituted $C_1-C_6$ alkyl wherein the substituent on the substituted $C_1-C_6$ alkyl is selected from unsubstituted or substituted phenyl, —$N(R^{10})_2$, $R^{10}O$— and $R^{10}C(O)NR^{10}$—.

Preferably, $R^2$ is selected from: H,

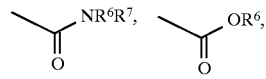

and an unsubstituted or substituted group, the group selected from $C_{1-8}$ alkyl, $C_{2-8}$ alkenyl and $C_{2-8}$ alkynyl;
wherein the substituted group is substituted with one or more of:
1) aryl or heterocycle, unsubstituted or substituted with:
   a) $C_{1-4}$ alkyl,
   b) $(CH_2)_pOR^6$,
   c) $(CH_2)_pNR^6R^7$,
   d) halogen,
2) $C_{3-6}$ cycloalkyl, 3) OR$^6$,
4) SR$^{6a}$, S(O)R$^{6a}$, SO$_2$R$^{6a}$,

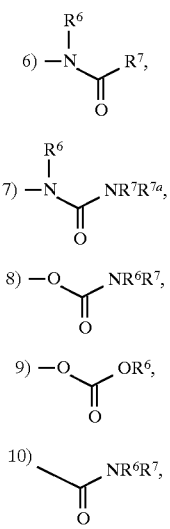

6) $-\underset{\underset{O}{\|}}{\overset{R^6}{N}}\diagdown\!\!\diagup R^7$,

7) $-\underset{\underset{O}{\|}}{\overset{R^6}{N}}\diagdown\!\!\diagup NR^7R^{7a}$, 8) $-\underset{\underset{O}{\|}}{O}\diagdown\!\!\diagup NR^6R^7$, 9) $-\underset{\underset{O}{\|}}{O}\diagdown\!\!\diagup OR^6$, 10) $\diagdown\!\!\underset{\underset{O}{\|}}{\phantom{O}}\!\!\diagup NR^6R^7$,

11) —SO$_2$—NR$^6$R$^7$,

12) $-\underset{}{\overset{R^6}{N}}-SO_2-R^{6a}$,

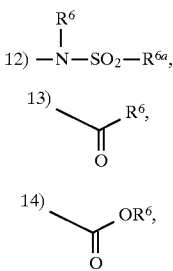

13) $\diagdown\!\!\underset{\underset{O}{\|}}{\phantom{O}}\!\!\diagup R^6$,

14) $\diagdown\!\!\underset{\underset{O}{\|}}{\phantom{O}}\!\!\diagup OR^6$,

15) N$_3$, or
16) F.

Preferably, R$^3$ is selected from: hydrogen and C$_1$–C$_6$ alkyl.

Preferably, R$^4$ and R$^5$ are hydrogen.

Preferably, R$^6$, R$^7$ and R$^{7a}$ is selected from: hydrogen, unsubstituted or substituted C$_1$–C$_6$ alkyl, unsubstituted or substituted aryl and unsubstituted or substituted cycloalkyl.

Preferably, R$_{6a}$ is unsubstituted or substituted C$_1$–C$_6$ alkyl, unsubstituted or substituted aryl and unsubstituted or substituted cycloalkyl.

Preferably, R$^9$ is hydrogen or methyl. Most preferably, R$^a$ is hydrogen.

Preferably, R$^{10}$ is selected from H, C$_1$–C$_6$ alkyl and benzyl.

Preferably, A$^1$ and A$^2$ are independently selected from: a bond, —C(O)NR$^{10}$—, —NR$^{10}$C(O)—, O, —N(R$^{10}$)—, —S(O)$_2$N(R$^{10}$)— and —N(R$^{10}$)S(O)$_2$—.

Preferably, V is selected from hydrogen, heterocycle and aryl. More preferably, V is phenyl.

Preferably, W is selected from imidazolinyl, imidazolyl, oxazolyl, pyrazolyl, pyyrolidinyl, thiazolyl and pyridyl. More preferably, W is selected from imidazolyl and pyridyl.

Preferably, X is —CH$_2$— or —C(O)—.

Preferably, Z is selected from unsubstituted or substituted phenyl, unsubstituted or substituted naphthyl, unsubstituted or substituted pyridyl, unsubstituted or substituted furanyl and unsubstituted or substituted thienyl. More preferably, Z is unsubstituted or substituted phenyl.

Preferably, n and r are independently 0, 1, or 2.

Preferably p is 1, 2 or 3.
Preferably s is 0.
Preferably t is 1.

Preferably, in compounds of the formula A, when X is —C(=O)—, or —S(=O)$_m$—, then t is 1 and the substitutent (R$^8$)$_r$— V—A$^1$(CR$^{1a}_2$)$_n$A$^2$(CR$^{1a}_2$)$_n$— is not H;

It is intended that the definition of any substituent or variable (e.g., R$^{1a}$, R$^9$, n, etc.) at a particular location in a molecule be independent of its definitions elsewhere in that molecule. Thus, —N(R$^{10}$)$_2$ represents —NHH, —NHCH$_3$, —NHC$_2$H$_5$, etc. It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials.

The pharmaceutically acceptable salts of the compounds of this invention include the conventional non-toxic salts of the compounds of this invention as formed, e.g., from non-toxic inorganic or organic acids. For example, such conventional non-toxic salts include those derived from inorganic acids such as hydrochloric, hydrobromic, sulfuric, sulfamic, phosphoric, nitric and the like: and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxy-benzoic, fumaric, toluenesulfonic, methanesulfonic, ethane disulfonic, oxalic, isethionic, trifluoroacetic and the like.

The pharmaceutically acceptable salts of the compounds of this invention can be synthesized from the compounds of this invention which contain a basic moiety by conventional chemical methods. Generally, the salts are prepared either by ion exchange chromatography or by reacting the free base with stoichiometric amounts or with an excess of the desired salt-forming inorganic or organic acid in a suitable solvent or various combinations of solvents.

Reactions used to generate the compounds of this invention are prepared by employing reactions as shown in the Schemes 1–14, in addition to other standard manipulations such as ester hydrolysis, cleavage of protecting groups, etc., as may be known in the literature or exemplified in the experimental procedures.

These reactions may be employed in a linear sequence to provide the compounds of the invention or they may be used to synthesize fragments which are subsequently joined by the alkylation reactions described in the Schemes.

Synopsis of Schemes 1–14:

The requisite intermediates are in some cases commercially available, or can be prepared according to literature procedures, for the most part. 2-Piperazinones can be generally prepared as shown in Scheme 1. Amination of the suitably substituted 2-oxazolidinone I provides the diamine II. This is then reacted with a suitably substituted bromoacetate to provide the secondary amide III; acid deprotection provides the key intermediate IV. Ring closure to the 2-piperazinones VI occurs concurrently with reductive alkylation with an aldehyde such as the protected imidazolyl aldehyde V. The imidazolyl protecting group may be removed under acidic conditions such as trifluoroacetic acid in methylene chloride. Alternatively, the imidazolyl may be alkylated and then deprotected to provide compounds such as VIII The intermediate IV can be cyclized and reductively alkylated with a variety of aldehydes, such as IX. The aldehydes can be prepared by standard procedures, such as that described by O. P. Goel, U. Krolls, M. Stier and S. Kesten in *Organic Syntheses*, 1988, 67, 69–75), from the appropriate amino acid (Scheme 2). The reductive alkylation can be accomplished at pH 5–7 with a variety of reducing agents, such as sodium triacetoxyborohydride or sodium cyanoborohydride in a solvent such as dichloroethane, methanol or dimethylformamide. The product X can be deprotected to give the final compounds XI with trifluoroacetic acid in methylene chloride. The final product XI is isolated in the salt form, for example, as a trifluoroacetate, hydrochloride or acetate salt, among others. The product diamine XI can further be selectively protected to obtain XII, which can subsequently be reductively alkylated with a second aldehyde to obtain XIII. Removal of the protecting group, and conversion to cyclized products such as the dihydroimidazole XV can be accomplished by literature procedures.

As shown in Scheme 3, the imidazole acetic acid XVI can be converted to the acetate XVII by standard procedures, and the protected imidazole XVIII can be first reacted with an alkyl halide, then treated with refluxing methanol to provide the regiospecifically alkylated imidazole acetic acid ester XIX. The ester is hydrolyzed and the acid converted to the acid chloride. Reaction with the suitably substituted lithium diketopiperazine XXI in the presence of condensing reagents such as 1-(3-dimethylaminopropyl)-3-ethylcarbodiimide (EDC) leads to acylated products such as XXII.

If the intermediate IV is cyclized/reductively alkylated with an aldehyde which also has a protected hydroxyl group, such as XXIII in Scheme 4, the protecting groups can be subsequently removed to unmask the hydroxyl group (Schemes 4, 5). The alcohol can be oxidized under standard conditions to e.g. an aldehyde, which can then be reacted with a variety of organometallic reagents such as Grignard reagents, to obtain secondary alcohols such as XXVII. In addition, the fully deprotected amino alcohol XXV can be reductively alkylated (under conditions described previously) with a variety of aldehydes to obtain secondary amines, such as XXIX (Scheme 5), or tertiary amines.

The Boc protected amino alcohol XXV can also be utilized to synthesize 2-aziridinylmethylpiperazines such as XXX (Scheme 6). Treating XXV with 1,1'-sulfonyldiimidazole and sodium hydride in a solvent such as dimethylformamide led to the formation of aziridine XXX. The aziridine reacted in the presence of a nucleophile, such as a thiol, in the presence of base to yield, after deprotection, the ring-opened product XXXII.

In addition, the intermediate IV can be reacted with aldehydes derived from amino acids such as O-alkylated tyrosines, according to standard procedures, to obtain compounds such as XXXV as shown in Scheme 7. When R' is an aryl group, XXXV can first be hydrogenated to unmask the phenol, and the amine group deprotected with acid to produce XXXVI. Alternatively, the amine protecting group in XXXV can be removed, and O-alkylated phenolic amines such as XXXVII produced.

Reaction Scheme 8 provides an illustrative example the synthesis of compounds of the instant invention wherein the substituents $R^4$ and $R^5$ are combined to form —$(CH_2)_u$—. For example, 1-aminocyclohexan-1-al XXXVIII can be converted to the intermediate IXL essentially according to the procedures outlined in Schemes 1 and 2. The intermediate IXL can be deprotected as before, and carried on to final products as described in Schemes 3–7. It is understood that reagents utilized to provide the imidazolylalkyl substituent may be readily replaced by other reagents well known in the art and readily available to provide other N-substituents on the piperazine.

Scheme 9 illustrates the use of an optionally substituted homoserine lactone XLII to prepare a Boc-protected intermediate XLIII. Intermediate XLIII may be deprotected and cyclized/reductively alkylated or acylated as illustrated in the previous Schemes. Alternatively, the hydroxyl moiety of diketopiperazine XLIV may be mesylated and displaced by a suitable nucleophile, such as the sodium salt of ethane thiol, to provide an the sulfide XLV. Diketopiperazine XLIV may also be oxidized to provide the carboxylic acid on diketopiperazine XLVI, which can be further utilized to form an ester or amide moiety.

Amino acids of the general formula XLVIII which have a sidechain not found in natural amino acids may be prepared by the reactions illustrated in Scheme 10 starting with the readily prepared imine XLVII.

Schemes 11–14 illustrate syntheses of suitably substituted aldehydes useful in the syntheses of the instant compounds wherein the variable W is present as a pyridyl moiety. Similar synthetic strategies for preparing alkanols that incorporate other heterocyclic moieties for variable W are also well known in the art.

SCHEME 1

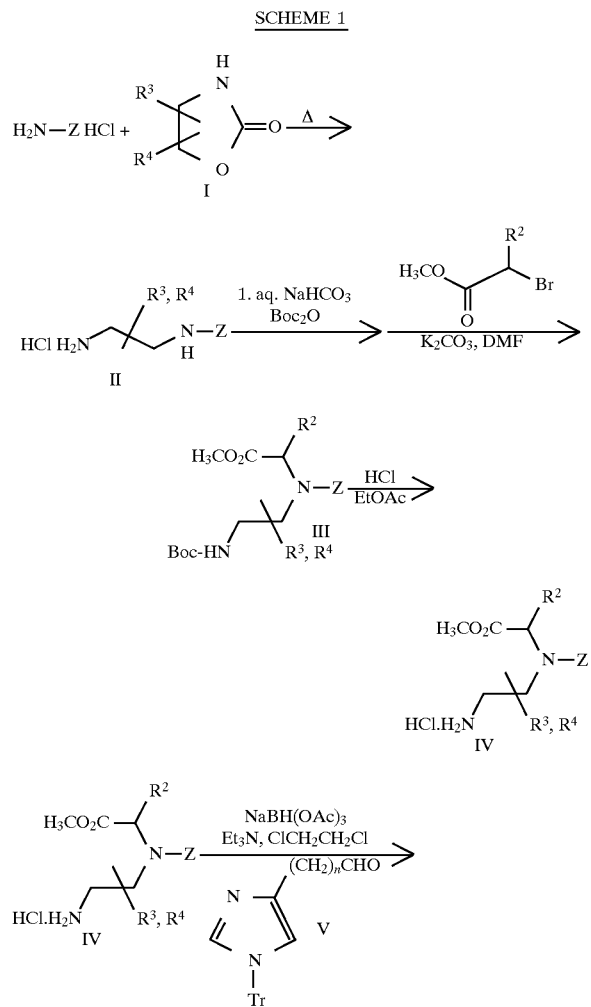

SCHEME 1
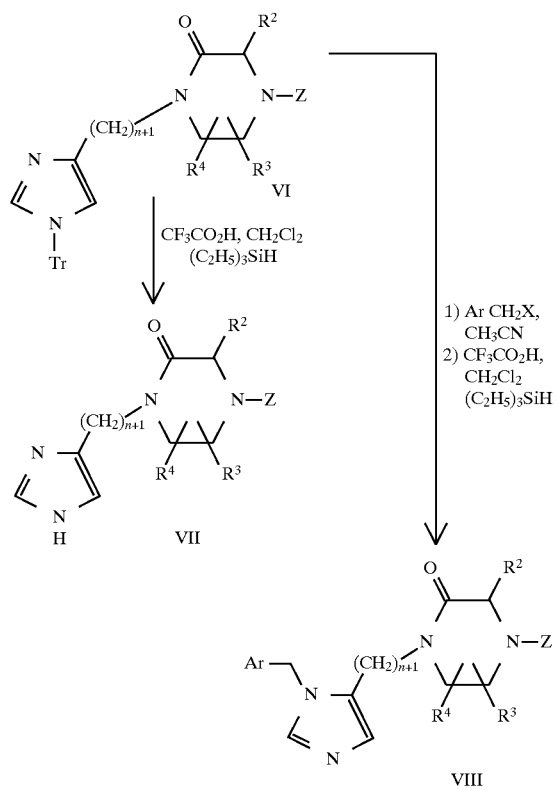
SCHEME 2
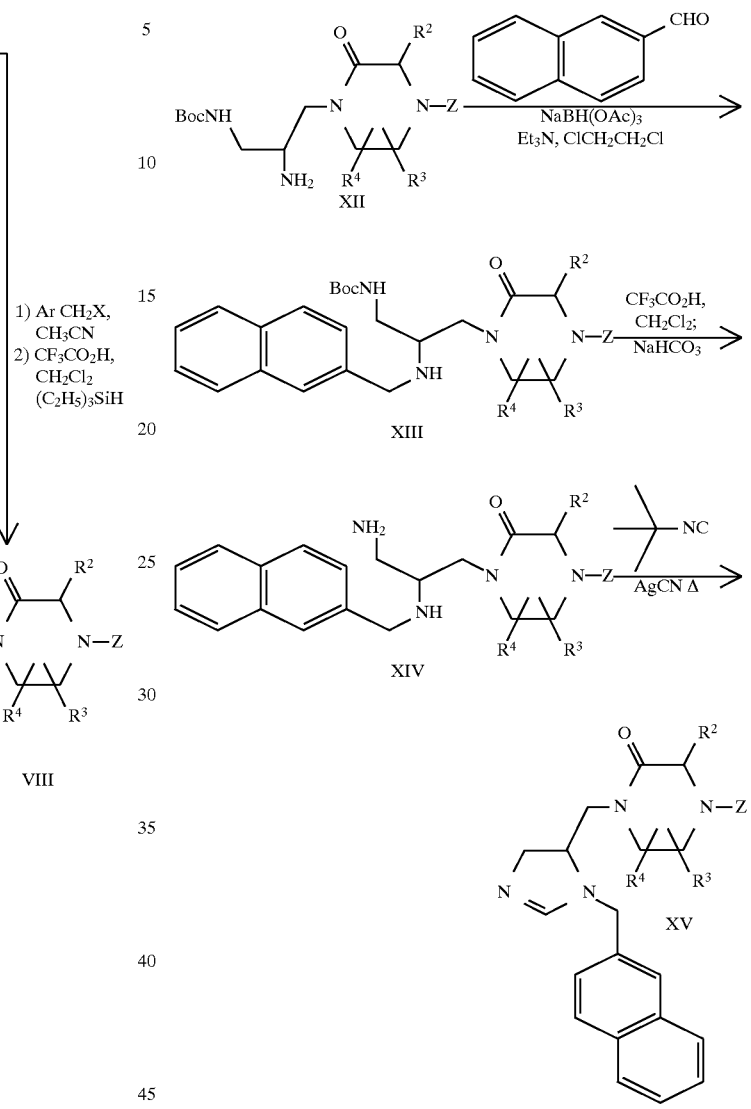
SCHEME 2
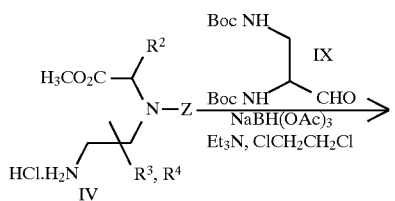
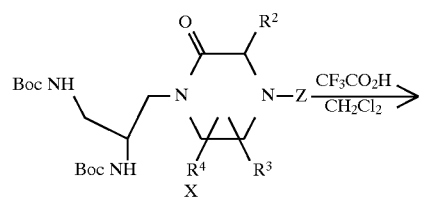
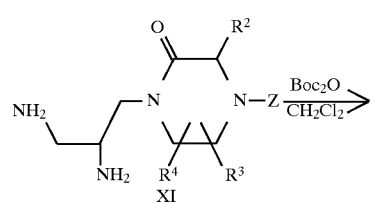
SCHEME 3
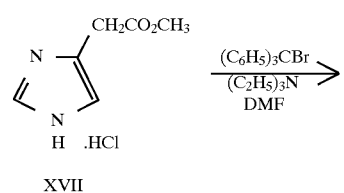

SCHEME 3
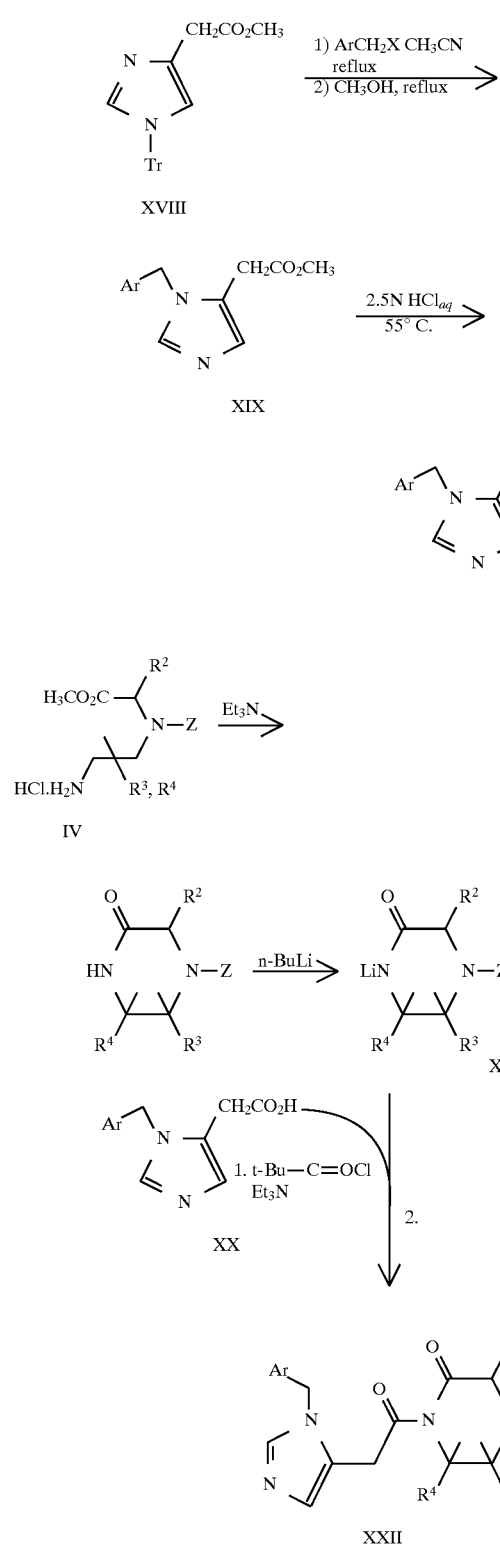
SCHEME 4
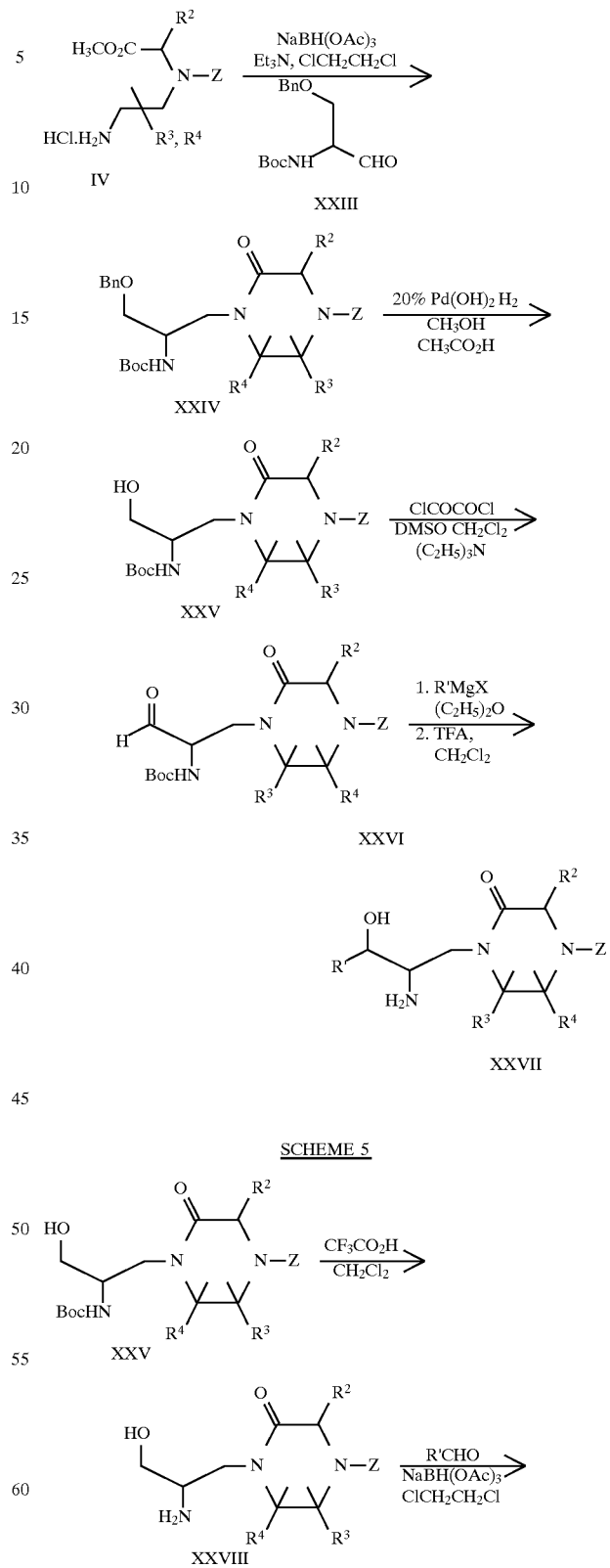
SCHEME 5
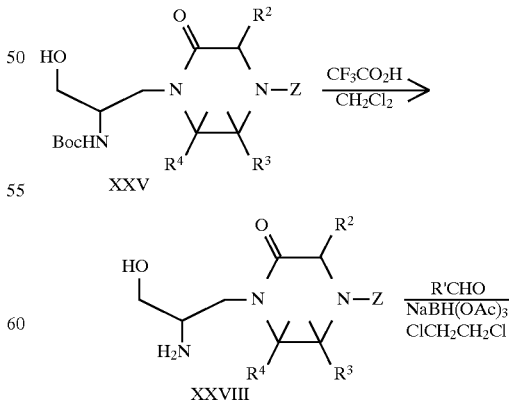

SCHEME 5 -continued
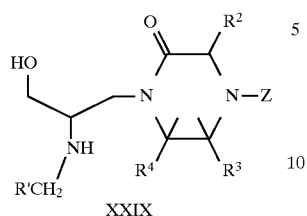
SCHEME 6
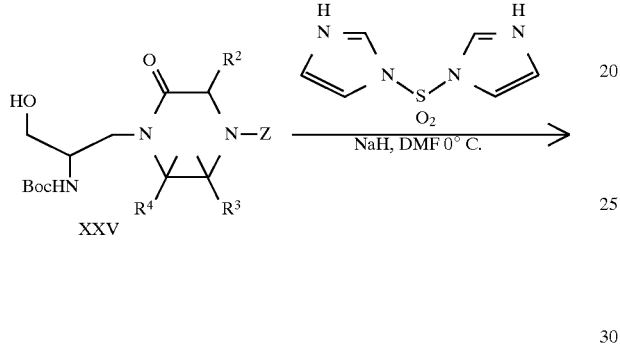
SCHEME 6 -continued
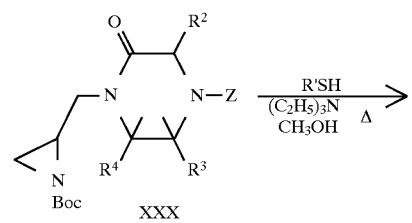
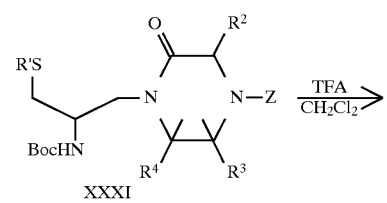
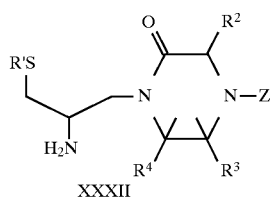
SCHEME 7
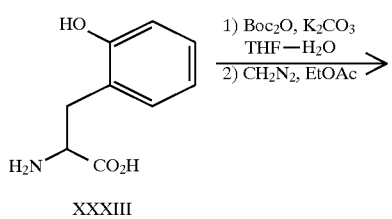
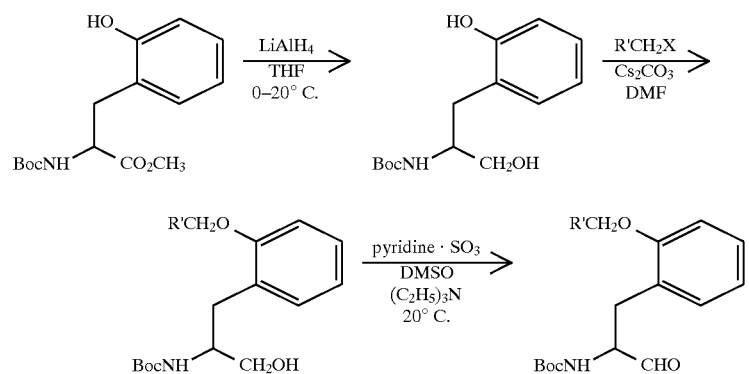

-continued
SCHEME 7
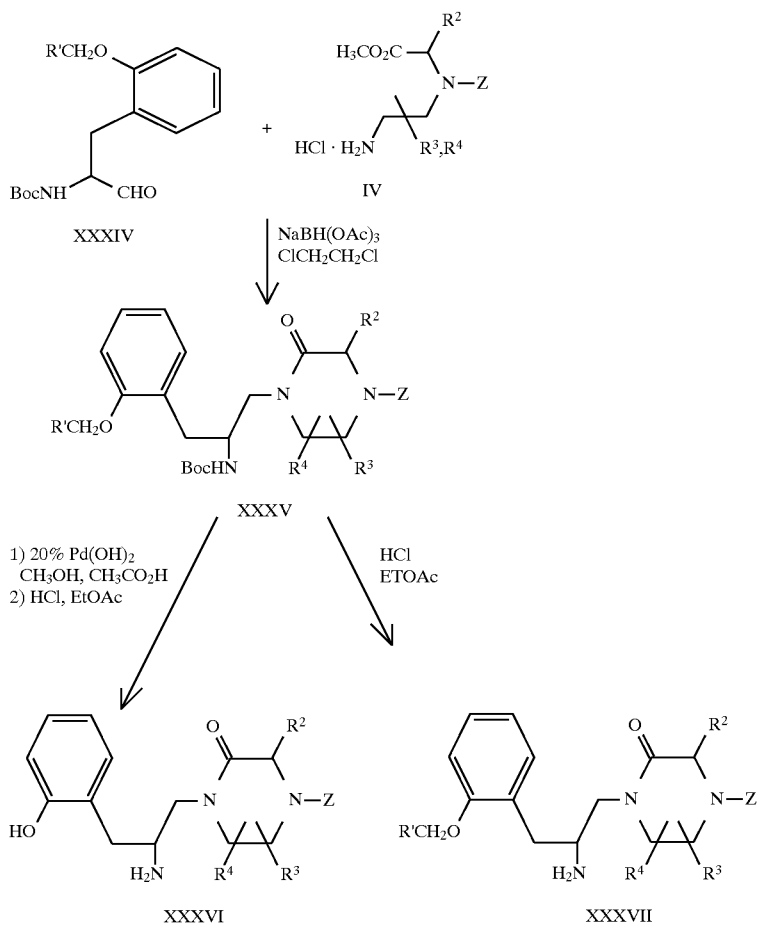
SCHEME 8
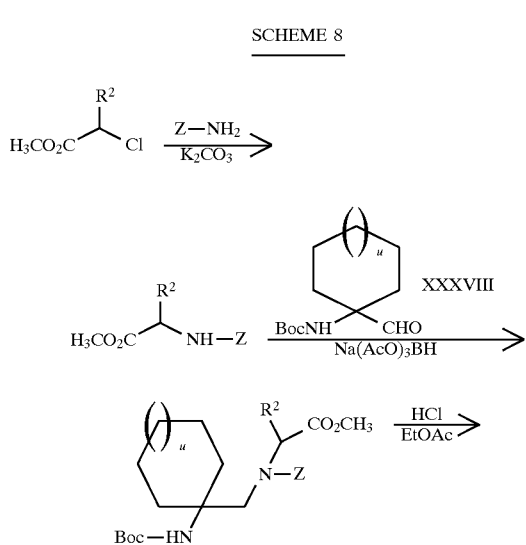
-continued
SCHEME 8
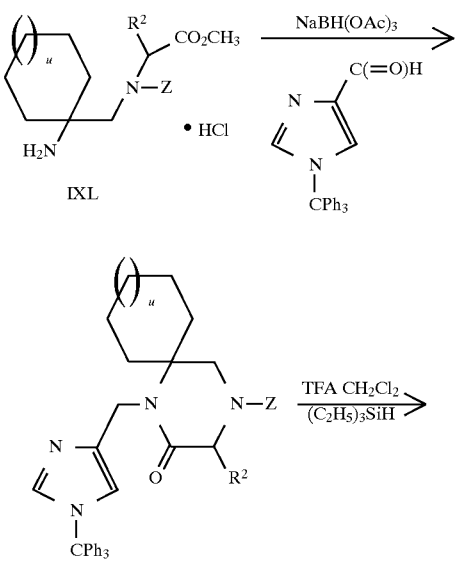

-continued
SCHEME 8
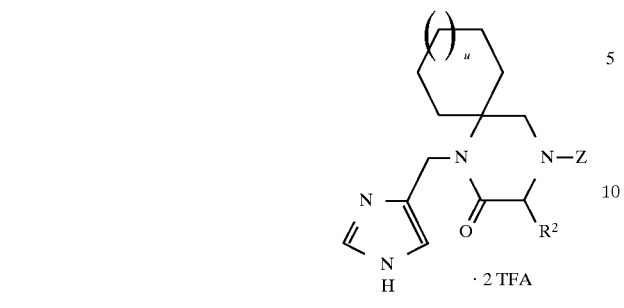
SCHEME 9
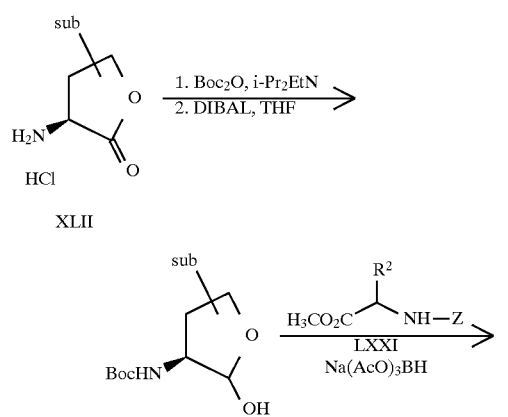
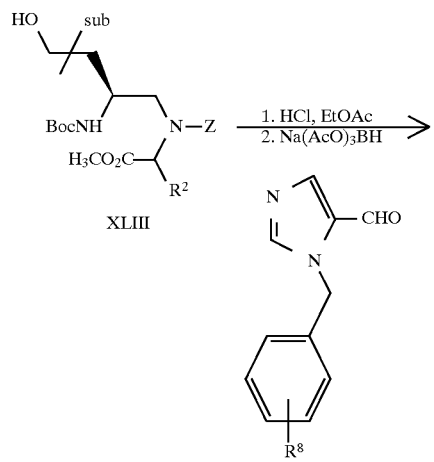
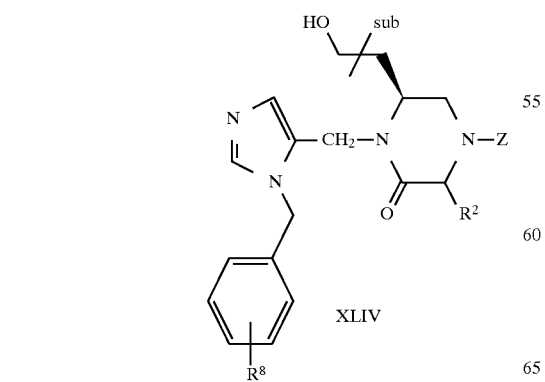
-continued
SCHEME 9
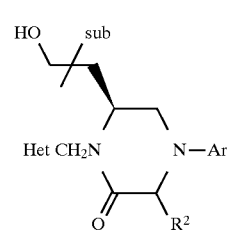
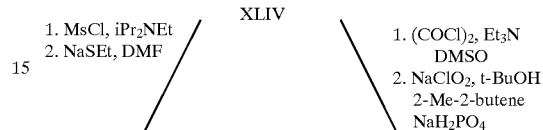
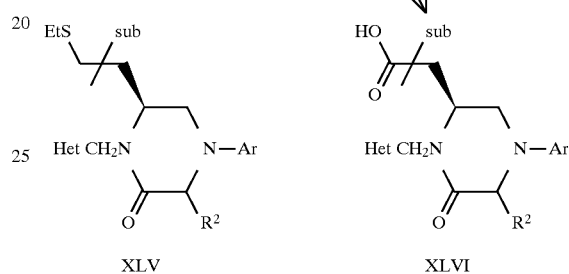
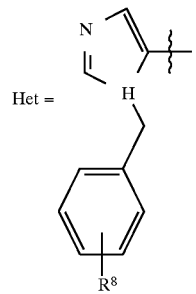
SCHEME 10
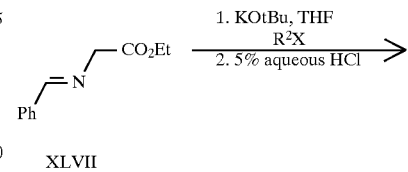
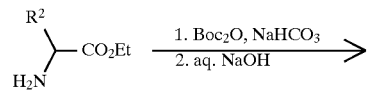
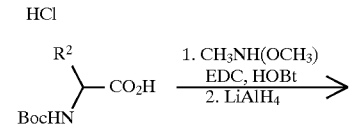
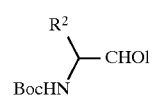

SCHEME 11
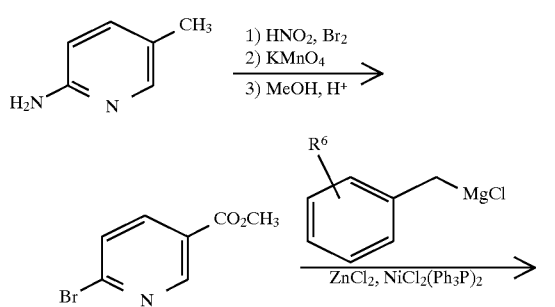
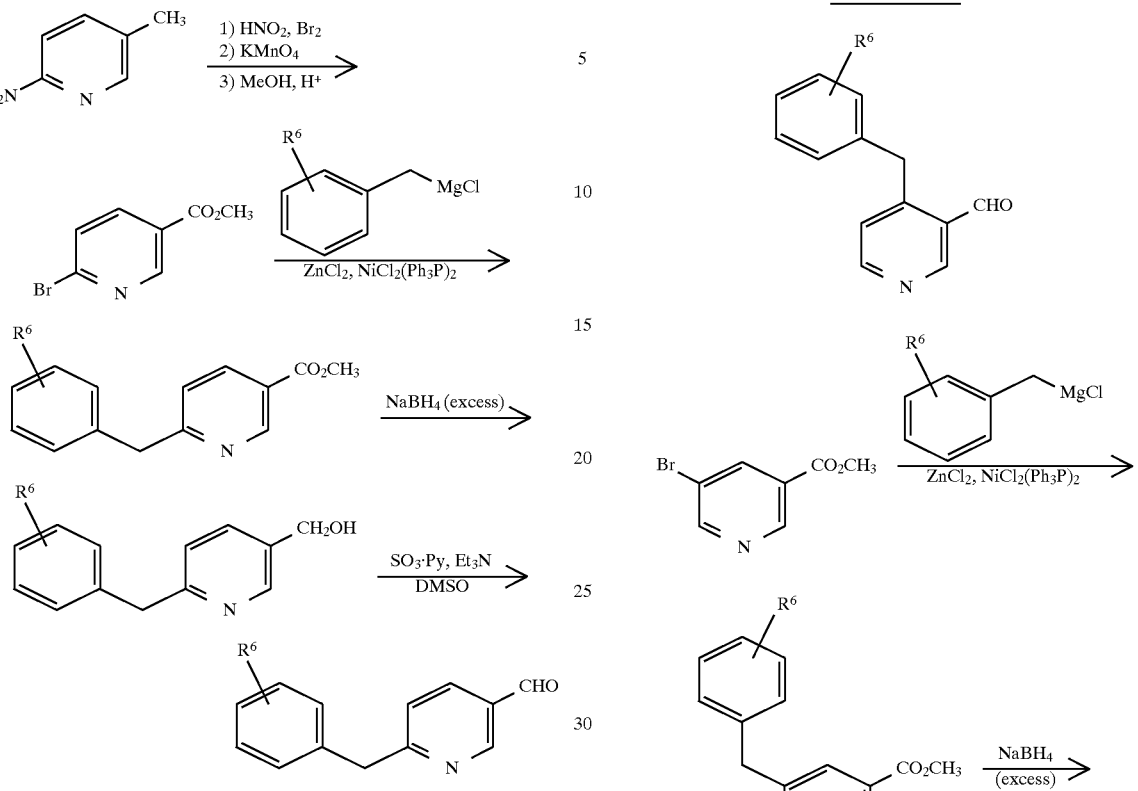
SCHEME 12
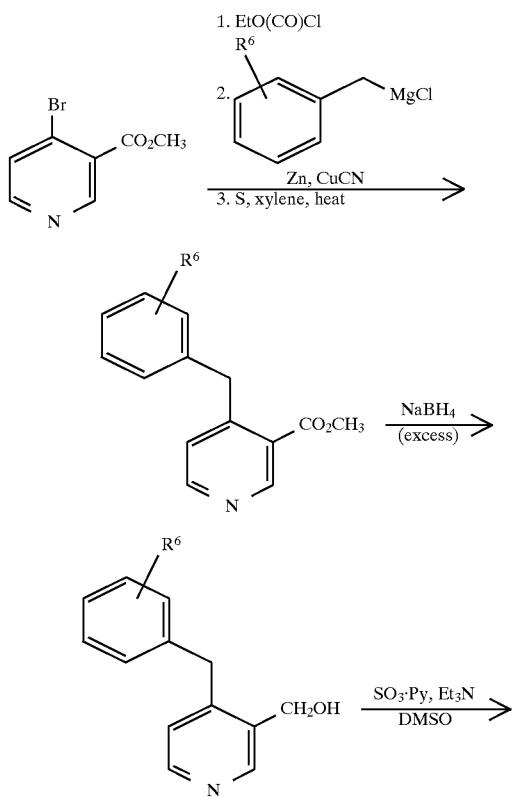
SCHEME 13
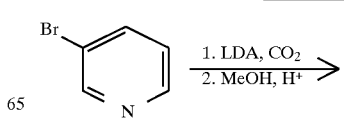

SCHEME 13 -continued

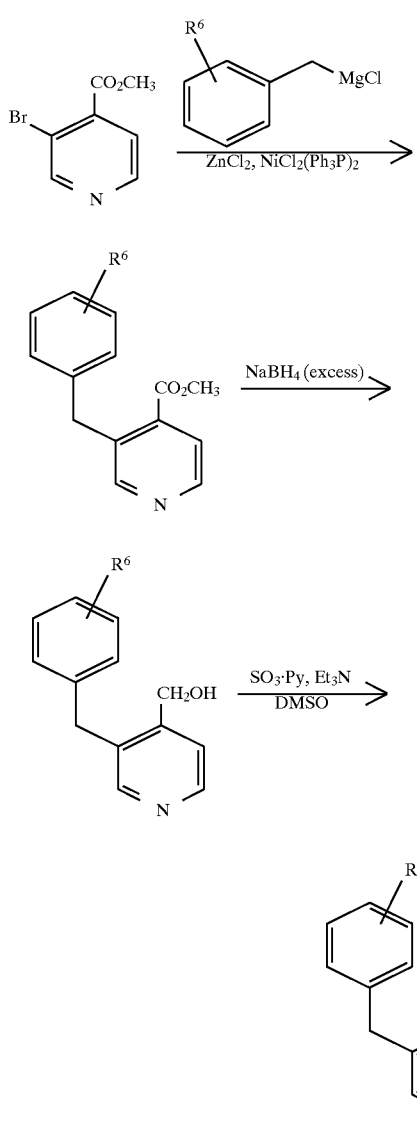

SCHEME 14

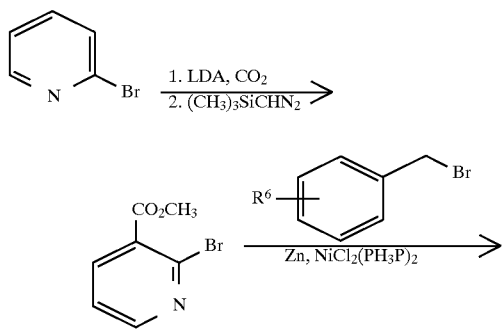

SCHEME 14 -continued

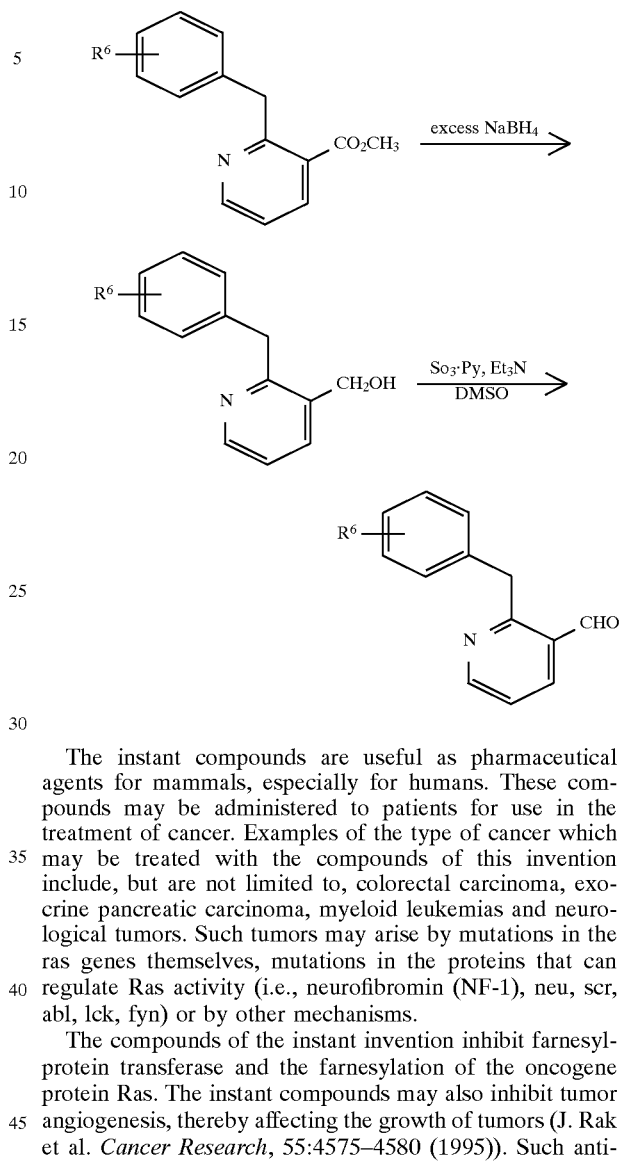

The instant compounds are useful as pharmaceutical agents for mammals, especially for humans. These compounds may be administered to patients for use in the treatment of cancer. Examples of the type of cancer which may be treated with the compounds of this invention include, but are not limited to, colorectal carcinoma, exocrine pancreatic carcinoma, myeloid leukemias and neurological tumors. Such tumors may arise by mutations in the ras genes themselves, mutations in the proteins that can regulate Ras activity (i.e., neurofibromin (NF-1), neu, scr, abl, lck, fyn) or by other mechanisms.

The compounds of the instant invention inhibit farnesyl-protein transferase and the farnesylation of the oncogene protein Ras. The instant compounds may also inhibit tumor angiogenesis, thereby affecting the growth of tumors (J. Rak et al. *Cancer Research*, 55:4575–4580 (1995)). Such anti-angiogenesis properties of the instant compounds may also be useful in the treatment of certain forms of blindness related to retinal vascularization.

The compounds of this invention are also useful for inhibiting other proliferative diseases, both benign and malignant, wherein Ras proteins are aberrantly activated as a result of oncogenic mutation in other genes (i.e., the Ras gene itself is not activated by mutation to an oncogenic form) with said inhibition being accomplished by the administration of an effective amount of the compounds of the invention to a mammal in need of such treatment. For example, a component of NF-1 is a benign proliferative disorder.

The instant compounds may also be useful in the treatment of certain viral infections, in particular in the treatment of hepatitis delta and related viruses (J. S. Glenn et al. *Science*, 256:1331–1333 (1992)).

The compounds of the instant invention are also useful in the prevention of restenosis after percutaneous transluminal coronary angioplasty by inhibiting neointimal formation (C. Indolfi et al. *Nature medicine*, 1:541–545(1995).

The instant compounds may also be useful in the treatment and prevention of polycystic kidney disease (D. L. Schaffner et al. *American Journal of Pathology*, 142:1051–1060 (1993) and B. Cowley, Jr. et al.*FASEB Journal*, 2:A3160 (1988)).

The instant compounds may also be useful for the treatment of fungal infections.

The compounds of this invention may be administered to mammals, preferably humans, either alone or, preferably, in combination with pharmaceutically acceptable carriers or diluents, optionally with known adjuvants, such as alum, in a pharmaceutical composition, according to standard pharmaceutical practice. The compounds can be administered orally or parenterally, including the intravenous, intramuscular, intraperitoneal, subcutaneous, rectal and topical routes of administration.

For oral use of a chemotherapeutic compound according to this invention, the selected compound may be administered, for example, in the form of tablets or capsules, or as an aqueous solution or suspension. In the case of tablets for oral use, carriers which are commonly used include lactose and corn starch, and lubricating agents, such as magnesium stearate, are commonly added. For oral administration in capsule form, useful diluents include lactose and dried corn starch. When aqueous suspensions are required for oral use, the active ingredient is combined with emulsifying and suspending agents. If desired, certain sweetening and/or flavoring agents may be added. For intramuscular, intraperitoneal, subcutaneous and intravenous use, sterile solutions of the active ingredient are usually prepared, and the pH of the solutions should be suitably adjusted and buffered. For intravenous use, the total concentration of solutes should be controlled in order to render the preparation isotonic.

The compounds of the instant invention may also be co-administered with other well known therapeutic agents that are selected for their particular usefulness against the condition that is being treated. For example, the instant compounds may be useful in combination with known anti-cancer and cytotoxic agents. Similarly, the instant compounds may be useful in combination with agents that are effective in the treatment and prevention of NF-1, restenosis, polycystic kidney disease, infections of hepatitis delta and related viruses and fungal infections.

If formulated as a fixed dose, such combination products employ the compounds of this invention within the dosage range described below and the other pharmaceutically active agent(s) within its approved dosage range. Compounds of the instant invention may alternatively be used sequentially with known pharmaceutically acceptable agent(s) when a combination formulation is inappropriate.

The present invention also encompasses a pharmaceutical composition useful in the treatment of cancer, comprising the administration of a therapeutically effective amount of the compounds of this invention, with or without pharmaceutically acceptable carriers or diluents. Suitable compositions of this invention include aqueous solutions comprising compounds of this invention and pharmacologically acceptable carriers, e.g., saline, at a pH level, e.g., 7.4. The solutions may be introduced into a patient's blood-stream by local bolus injection.

When a compound according to this invention is administered into a human subject, the daily dosage will normally be determined by the prescribing physician with the dosage generally varying according to the age, weight, and response of the individual patient, as well as the severity of the patient's symptoms.

In one exemplary application, a suitable amount of compound is administered to a mammal undergoing treatment for cancer. Administration occurs in an amount between about 0.1 mg/kg of body weight to about 60 mg/kg of body weight per day, preferably of between 0.5 mg/kg of body weight to about 40 mg/kg of body weight per day.

The compounds of the instant invention are also useful as a component in an assay to rapidly determine the presence and quantity of farnesyl-protein transferase (FPTase) in a composition. Thus the composition to be tested may be divided and the two portions contacted with mixtures which comprise a known substrate of FPTase (for example a tetrapeptide having a cysteine at the amine terminus) and farnesyl pyrophosphate and, in one of the mixtures, a compound of the instant invention. After the assay mixtures are incubated for an sufficient period of time, well known in the art, to allow the FPTase to farnesylate the substrate, the chemical content of the assay mixtures may be determined by well known immunological, radiochemical or chromatographic techniques. Because the compounds of the instant invention are selective inhibitors of FPTase, absence or quantitative reduction of the amount of substrate in the assay mixture without the compound of the instant invention relative to the presence of the unchanged substrate in the assay containing the instant compound is indicative of the presence of FPTase in the composition to be tested.

It would be readily apparent to one of ordinary skill in the art that such an assay as described above would be useful in identifying tissue samples which contain farnesyl-protein transferase and quantitating the enzyme. Thus, potent inhibitor compounds of the instant invention may be used in an active site titration assay to determine the quantity of enzyme in the sample. A series of samples composed of aliquots of a tissue extract containing an unknown amount of farnesyl-protein transferase, an excess amount of a known substrate of FPTase (for example a tetrapeptide having a cysteine at the amine terminus) and farnesyl pyrophosphate are incubated for an appropriate period of time in the presence of varying concentrations of a compound of the instant invention. The concentration of a sufficiently potent inhibitor (i.e., one that has a Ki substantially smaller than the concentration of enzyme in the assay vessel) required to inhibit the enzymatic activity of the sample by 50% is approximately equal to half of the concentration of the enzyme in that particular sample.

EXAMPLES

Examples provided are intended to assist in a further understanding of the invention. Particular materials employed, species and conditions are intended to be further illustrative of the invention and not limitative of the reasonable scope thereof.

Example 1

4-(3-Chlorophenyl)-1-[1-(4-cyanobenzyl)-5-imidazolylmethyl]-2-piperazinone hydrochloride Step A: Preparation of 1-triphenylmethyl-4-(hydroxymethyl)-imidazole To a solution of 4-(hydroxymethyl)imidazole hydrochloride (35.0 g, 260 mmol) in 250 mL of dry DMF at room temperature was added triethylamine (90.6 mL, 650 mmol). A white solid precipitated from the solution. Chlorotriphenylmethane (76.1 g, 273 mmol) in 500 mL of DMF was added dropwise. The reaction mixture was stirred for 20

39 hours, poured over ice, filtered, and washed with ice water. The resulting product was slurried with cold dioxane, filtered, and dried in vacuo to provide the titled product as a white solid which was sufficiently pure for use in the next step.

Step B: Preparation of 1-triphenylmethyl-4-(acetoxymethyl)-imidazole

Alcohol from Step A (260 mmol, prepared above) was suspended in 500 mL of pyridine. Acetic anhydride (74 mL, 780 mmol) was added dropwise, and the reaction was stirred for 48 hours during which it became homogeneous. The solution was poured into 2 L of EtOAc, washed with water (3×1 L), 5% aq. HCl soln. (2×1 L), sat. aq. NaHCO$_3$, and brine, then dried (Na$_2$SO$_4$), filtered, and concentrated in vacuo to provide the crude product. The acetate was isolated as a white powder (85.8 g, 86% yield for two steps) which was sufficiently pure for use in the next reaction.

Step C: Preparation of 1-(4-cyanobenzyl)-5-(acetoxymethyl)-imidazole hydrobromide A solution of the product from Step B (85.8 g, 225 mmol) and α-bromo-p-tolunitrile (50.1 g, 232 mmol) in 500 mL of EtOAc was stirred at 60° C. for 20 hours, during which a pale yellow precipitate formed. The reaction was cooled to room temperature and filtered to provide the solid imidazolium bromide salt. The filtrate was concentrated in vacuo to a volume 200 mL, reheated at 60° C. for two hours, cooled to room temperature, and filtered again. The filtrate was concentrated in vacuo to a volume 100 mL, reheated at 60° C. for another two hours, cooled to room temperature, and concentrated in vacuo to provide a pale yellow solid. All of the solid material was combined, dissolved in 500 mL of methanol, and warmed to 60° C. After two hours, the solution was reconcentrated in vacuo to provide a white solid which was triturated with hexane to remove soluble materials. Removal of residual solvents in vacuo provided the titled product hydrobromide as a white solid (50.4 g, 67% yield, 89% purity by HPLC) which was used in the next step without further purification.

Step D: Preparation of 1-(4-cyanobenzyl)-5-(hydroxymethyl)-imidazole

To a solution of the acetate from Step C (50.4 g, 150 mmol) in 1.5 L of 3:1 THF/water at 0° C. was added lithium hydroxide monohydrate (18.9 g, 450 mmol). After one hour, the reaction was concentrated in vacuo, diluted with EtOAc (3 L), and washed with water, sat. aq. NaHCO$_3$ and brine. The solution was then dried (Na$_2$SO$_4$), filtered, and concentrated in vacuo to provide the crude product (26.2 g, 82% yield) as a pale yellow fluffy solid which was sufficiently pure for use in the next step without further purification.

Step E: Preparation of 1-(4-cyanobenzyl)-5-imidazole-carboxaldehyde

To a solution of the alcohol from Step D (21.5 g, 101 mmol) in 500 mL of DMSO at room temperature was added triethylamine (56 mL, 402 mmol), then SO$_3$-pyridine complex (40.5 g, 254 mmol). After 45 minutes, the reaction was poured into 2.5 L of EtOAc, washed with water (4×1 L) and brine, dried (Na$_2$SO$_4$), filtered, and concentrated in vacuo to provide the aldehyde (18.7 g, 88% yield) as a white powder which was sufficiently pure for use in the next step without further purification.

Step F: Preparation of N-(3-chlorophenyl)ethylenediamine hydrochloride

To a solution of 3-chloroaniline (30.0 mL, 284 mmol) in 500 mL of dichloromethane at 0° C. was added dropwise a solution of 4N HCl in 1,4-dioxane (80 mL, 320 mmol HCl). The solution was warmed to room temperature, then concentrated to dryness in vacuo to provide a white powder. A mixture of this powder with 2-oxazolidinone (24.6 g, 282 mmol) was heated under nitrogen atmosphere at 160° C. for 10 hours, during which the solids melted, and gas evolution was observed. The reaction was allowed to cool, forming the crude diamine hydrochloride salt as a pale brown solid.

Step G: Preparation of N-(tert-butoxycarbonyl)-N'-(3-chlorophenyl)ethylenediamine The amine hydrochloride from Step F (ca. 282 mmol, crude material prepared above) was taken up in 500 mL of THF and 500 mL of sat. aq. NaHCO$_3$ soln., cooled to 0° C., and di-tert-butylpyrocarbonate (61.6 g, 282 mmol) was added. After 30 h, the reaction was poured into EtOAc, washed with water and brine, dried (Na$_2$SO$_4$), filtered, and concentrated in vacuo to provide the titled carbamate (77 g, 100% yield for two steps, ca. 80% pure by $^1$H NMR) as a brown oil which was used in the next step without further purification.

Step H: Preparation of N-[2-(tert-butoxycarbamoyl)ethyl]-N-[(carbomethoxy)methyl]-3-chloroaniline To a solution of the product from Step G (1.06 g, 3.93 mmol) and potassium carbonate (804 mg, 5.82 mmol) in 10 mL of DMF was added methylbromoacetate (0.409 mL, 4.32 mmol), and the reaction was stirred at room temperature. After 1 h, another portion of methylbromoacetate (0.40 mL) was added, and the solution was warmed to 60° C. Two more portions of methylbromoacetate (0.40 mL) were added after 5 hours and 7 hours, and the reaction was stirred overnight. After 20 hours, the reaction was poured into EtOAc and washed with water, sat. aq. NaHCO$_3$ soln., and brine. The solution was dried (Na$_2$SO$_4$), filtered, and concentrated in vacuo. The resulting material was purified by silica gel chromatography (30–50% EtOAc/hexane) to provide the titled compound (1.19 g) as a pale yellow oil.

Step I: Preparation of N-(2-aminoethyl)-N-[(carbomethoxy)-methyl]-3-chloroaniline hydrochloride Through a solution of Boc-protected amine from Step H (1.19 g) in 20 mL of EtOAc at 0° C. was bubbled anhydrous HCl gas. After 4 hours, nitrogen gas was bubbled through the reaction to remove excess HCl, and the mixture was warmed to room temperature. The solution was concentrated in vacuo to provide the titled hydrochloride (0.920 g) as an orange foam which was used in the next step without further purification.

Step J: Preparation of 4-(3-chlorophenyl)-1-[1-(4-cyanobenzyl)-5-imidazolylmethyl]-2-piperazinone hydrochloride To a solution of the amine hydrochloride from Step I (532 mg, 1.91 mmol) in 5 mL of 1,2-dichloroethane at 0° C. was added 4 Å powdered molecular sieves (0.9 g), followed by sodium triacetoxyborohydride (614 mg, 2.91 mmol). The aldehyde from Step E (446 mg, 2.11 mmol) was added, and the reaction was stirred overnight, allowing it to warm to room temperature. After 20 hours, the reaction was poured into EtOAc, washed with sat. aq. NaHCO$_3$, and brine, dried (Na$_2$SO$_4$), filtered, and concentrated in vacuo. The resulting product was taken up in 10 mL of CH$_2$Cl$_2$, and propylamine (3 mL) was added. The reaction was stirred for 4 hours, then concentrated in vacuo, and purified by silica gel chromatography (50–80% acetone/hexane), then taken up in CH$_2$Cl$_2$ and treated with excess 1M HCl/ether solution, and concentrated in vacuo. The titled product hydrochloride (335 mg) was isolated as a white solid.

FAB mass spectrum m/e 406 (M+1). Analysis calculated for C$_{22}$H$_{20}$ClN$_5$O·1.50 HCl·1.40 H$_2$O: C, 54.39; H, 5.04; N, 14.42; Found: C, 54.51; H, 5.04; N, 13.60.

Example 2

(S)-6-n-Butyl-1-[1-(4-cyanobenzyl)-5-imidazolylmethyl]-4-(2,3-dimethylphenyl)-2-piperazinone hydrochloride Step A: Preparation of N-Methoxy-N-methyl 2(S)-(tert-butoxycarbonylamino)-hexanamide 2(S)-Butoxycarbonylaminohexanoic acid (24.6 g, 0.106 mol), N,O-dimethylhydroxylamine hydrochloride (15.5 g, 0.15 mol), EDC hydrochloride (22.3 g, 0.117 mol) and HOBT (14.3 g, 0.106 mol) were stirred in dry, degassed DMF (300 mL) at 20° C. under nitrogen. N-Methylmorpholine was added to obtain pH 7. The reaction was stirred overnight, the DMF distilled under high vacuum, and the residue partitioned between ethyl acetate and 2% potassium hydrogen sulfate. The organic phase was washed with saturated sodium bicarbonate, water, and saturated brine, and dried with magnesium sulfate. The solvent was removed in vacuo to give the title compound.

Step B: Preparation of 2(S)-(tert-Butoxycarbonylamino)hexanal

A mechanically stirred suspension of lithium aluminum hydride (5.00 g, 0.131 mol) in ether (250 mL) was cooled to −45° C. under nitrogen. A solution of the product from Step A (28.3 g, 0.103 mol) in ether (125 mL) was added, maintaining the temperature below −35° C. When the addition was complete, the reaction was warmed to 5° C., then recooled to −45° C. A solution of potassium hydrogen sulfate (27.3 g, 0.200 mol) in water was slowly added, maintaining the temperature below −5° C. After quenching, the reaction was stirred at room temperature for 1 h. The mixture was filtered through Celite, the ether evaporated, and the remainder partitioned between ethyl acetate and 2% potassium hydrogen sulfate. After washing with saturated brine, drying over magnesium sulfate and solvent removal, the title compound was obtained.

Step C: Preparation of N-(2,3-Dimethylphenyl)-2(S)-(tert-butoxycarbonylamino)hexanamine 2,3-Dimethylaniline (8.32 mL, 68.3 mmol) was dissolved in dichloroethane under nitrogen. Acetic acid was added to obtain pH 5, and sodium triacetoxyborohydride (17.2 g, 80.8 mmol) and crushed molecular sieves (4 g) were added. A solution of the product from Step B (13.3 g, 62.1 mmol) in dichloroethane (80 mL) was added slowly dropwise at 20° C. The reaction was stirred overnight, then quenched with saturated sodium bicarbonate solution. The aqueous layer was removed, the organic phase washed with saturated brine and dried over magnesium sulfate. Crystallization from hexane gave the title compound.

Step D: Preparation of (S)-6-n-butyl-1-[1-(4-cyanobenzyl)-5-imidazolylmethyl]-4-(2,3-dimethylphenyl)-2-piperazinone hydrochloride The titled compound is prepared from the product of Step C using the procedures in Steps H, I, and J of Example 1. The product is purified by silica gel chromatography, then taken up in $CH_2Cl_2$ and treated with excess 1M HCl/ether solution, and concentrated in vacuo to provide the titled product hydrochloride.

Example 3

4-(3-Chlorophenyl)-1-[(3-(4-cyanobenzyl)pyridin-4-yl)methyl]-2-piperazinone hydrochloride Step A: Preparation of 3-(4-Cyanobenzyl)pyridin-4-carboxylic acid methyl ester A solution of 4-cyanobenzyl bromide (625 mg, 3.27 mmol) in dry THF (4mL) was added slowly over ~3 min. to a suspension of activated Zn (dust; 250 mg) in dry THF (2 mL) at 0° under an argon atmosphere. The ice-bath was removed and the slurry was stirred at room temperature for a further 30 min. Then 3-bromopyridin-4-carboxylic acid methyl ester (540 mg. 2.5 mmol) followed by dichlorobis(triphenylphosphine)nickel (II) (50 mg). The resultant reddish-brown mixture was stirred for 3 h at ~40°–45° C. The mixture was cooled and distributed between EtOAc (100 ml) and 5% aqueous citric acid (50 mL). The organic layer was washed with $H_2O$ (2×50 mL), dried with $Na_2SO_4$. After evaporation of the solvent the residue was purified on silica gel, eluting with 35% EtOAc in hexane to give 420 mg as a clear gum. FAB ms (M+1) 253.

Step B: Preparation of 3-(4-Cyanobenzyl)-4-(hydroxymethyl)-pyridine

The title compound was obtained by sodium borohydride (300 mg) reduction of the ester from Step A (415 mg) in methanol (5 mL) at room temperature. After stirring for 4 h the solution was evaporated and the product was purified on silica gel, eluting with 2% methanol in chloroform to give the title compound. FAB ms (M+1) 225.

Step C: Preparation of 3-(4-Cyanobenzyl)-4-pyridinal

The title compound was obtained by activated manganese dioxide (1.0 g) oxidation of the alcohol from Step B (240 mg, 1.07 mmol) in dioxane (10 mL) at reflux for 30 min. Filtration and evaporation of the solvent provided title compound, mp 80°–83° C.

Step D: Preparation of 4-(3-chlorophenyl)-1-[(3-(4-cyanobenzyl)pyridin-4-yl)methyl]-2-piperazinone hydrochloride The titled compound is prepared from the pyridinal from Step C and the amine hydrochloride from Step I of Example 1 using the reductive alkylation procedured in Step J of Example I. The product is purified by silica gel chromatography, then taken up in $CH_2Cl_2$ and treated with excess 1M HCl/ether solution, and concentrated in vacuo to provide the titled product hydrochloride.

Example 4

In vitro inhibition of ras farnesyl transferase

Assays of farnesyl-protein transferase. Partially purified bovine FPTase and Ras peptides (Ras-CVLS, Ras-CVIM and Ras-CAIL) were prepared as described by Schaber et al., *J. Biol. Chem.* 265:14701–14704 (1990), Pompliano, et al., *Biochemistry* 31:3800 (1992) and Gibbs et al., *PNAS* U.S.A. 86:6630–6634 (1989), respectively. Bovine FPTase was assayed in a volume of 100 $\mu$l containing 100 mM N-(2-hydroxy ethyl) piperazine-N'-(2-ethane sulfonic acid) (HEPES), pH 7.4, 5 mM $MgCl_2$, 5 mM dithiothreitol (DTT), 100 mM [$^3$H]-farnesyl diphosphate ([$^3$H]-FPP; 740 CBq/mmol, New England Nuclear), 650 nM Ras-CVLS and 10 $\mu$g/ml FPTase at 31° C. for 60 min. Reactions were initiated with FPTase and stopped with 1 ml of 1.0M HCL in ethanol. Precipitates were collected onto filter-mats using a TomTec Mach II cell harvestor, washed with 100% ethanol, dried and counted in an LKB β-plate counter. The assay was linear with respect to both substrates, FPTase levels and time; less than 10% of the [$^3$H]-FPP was utilized during the reaction period. Purified compounds were dissolved in 100% dimethyl sulfoxide (DMSO) and were diluted 20-fold into the assay. Percentage inhibition is measured by the amount of incorporation of radioactivity in the presence of the test compound when compared to the amount of incorporation in the absence of the test compound.

Human FPTase was prepared as described by Omer et al., *Biochemistry* 32:5167–5176 (1993). Human FPTase activity was assayed as described above with the exception that 0.1% (w/v) polyethylene glycol 20,000, 10 $\mu$M $ZnCl_2$ and 100 nM Ras-CVIM were added to the reaction mixture. Reactions were performed for 30 min., stopped with 100 $\mu$l of 30% (v/v) trichloroacetic acid (TCA) in ethanol and processed as described above for the bovine enzyme.

The compounds of the instant invention described Example 1 was tested for inhibitory activity against human FPTase by the assay described above and were found to have $IC_{50}$ of $\leq$10 $\mu$M.

Example 5

In vivo ras farnesylation assay

The cell line used in this assay is a v-ras line derived from either Rat1 or NIH3T3 cells, which expressed viral Ha-ras p21. The assay is performed essentially as described in DeClue, J. E. et al., *Cancer Research* 51:712–717, (1991). Cells in 10 cm dishes at 50–75% confluency are treated with the test compound (final concentration of solvent, methanol or dimethyl sulfoxide, is 0.1%). After 4 hours at 37° C., the cells are labelled in 3 ml methionine-free DMEM supplemeted with 10% regular DMEM, 2% fetal bovine serum and 400 mCi[$^{35}$S]methionine (1000 Ci/mmol). After an additional 20 hours, the cells are lysed in 1 ml lysis buffer (1% NP40/20 mM HEPES, pH 7.5/5 mM MgCl$_2$/1 mM DTT/10 mg/ml aprotinen/2 mg/ml leupeptin/2 mg/ml antipain/0.5 mM PMSF) and the lysates cleared by centrifugation at 100,000×g for 45 min. Aliquots of lysates containing equal numbers of acid-precipitable counts are bought to 1 ml with IP buffer (lysis buffer lacking DTT) and immunoprecipitated with the ras-specific monoclonal antibody Y13-259 (Furth, M. E. et al., *J. Virol.* 43:294–304, (1982)). Following a 2 hour antibody incubation at 4° C., 200 ml of a 25% suspension of protein A-Sepharose coated with rabbit anti rat IgG is added for 45 min. The immunoprecipitates are washed four times with IP buffer (20 nM HEPES, pH 7.5/1 mM EDTA/1% Triton X-100.0.5% deoxycholate/0.1%/SDS/0.1M NaCl) boiled in SDS-PAGE sample buffer and loaded on 13% acrylamide gels. When the dye front reached the bottom, the gel is fixed, soaked in Enlightening, dried and autoradiographed. The intensities of the bands corresponding to farnesylated and nonfarnesylated ras proteins are compared to determine the percent inhibition of farnesyl transfer to protein.

Example 6

In vivo growth inhibition assay

To determine the biological consequences of FPTase inhibition, the effect of the compounds of the instant invention on the anchorage-independent growth of Rat1 cells transformed with either a v-ras, v-raf, or v-mos oncogene is tested. Cells transformed by v-Raf and v-Mos maybe included in the analysis to evaluate the specificity of instant compounds for Ras-induced cell transformation.

Rat 1 cells transformed with either v-ras, v-raf, or v-mos are seeded at a density of $1\times10^4$ cells per plate (35 mm in diameter) in a 0.3% top agarose layer in medium A (Dulbecco's modified Eagle's medium supplemented with 10% fetal bovine serum) over a bottom agarose layer (0.6%). Both layers contain 0.1% methanol or an appropriate concentration of the instant compound (dissolved in methanol at 1000 times the final concentration used in the assay). The cells are fed twice weekly with 0.5 ml of medium A containing 0.1% methanol or the concentration of the instant compound. Photomicrographs are taken 16 days after the cultures are seeded and comparisons are made.

What is claimed is:

1. A compound which inhibits farnesyl-protein transferase of the formula A:

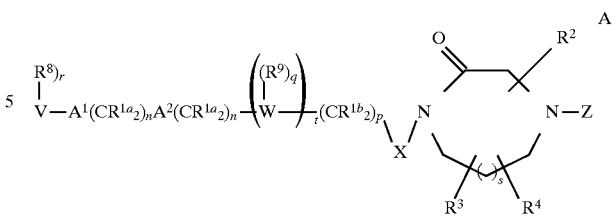

wherein:

$R^{1a}$ and $R^{1b}$ are independently selected from:
 a) hydrogen,
 b) aryl, $C_3$–$C_{10}$ cycloalkyl, $C_2$–$C_6$ alkenyl, $C_2$–$C_6$ alkynyl, $R^{10}O$—, $R^{11}S(O)_m$—, $R^{10}C(O)NR^{10}$—, $(R^{10})_2NC(O)$—, $R^{10}{}_2N$—$C(NR^{10})$—, CN, NO$_2$, $R^{10}C(O)$—, $N_3$, —$N(R^{10})_2$, or $R^{11}OC(O)NR^{10}$—,
 c) unsubstituted or substituted $C_1$–$C_6$ alkyl wherein the substitutent on the substituted $C_1$–$C_6$ alkyl is selected from unsubstituted or substituted aryl, $C_3$–$C_{10}$ cycloalkyl, $C_2$–$C_6$ alkenyl, $C_2$–$C_6$ alkynyl, $R^{10}O$—, $R^{11}S(O)_m$—, $R^{10}C(O)NR^{10}$—, $(R^{10})_2NC(O)$—, $R^{10}{}_2N$—$C(NR^{10})$—, CN, $R^{10}C(O)$—, $N_3$, —$N(R^{10})_2$, and $R^{11}OC(O)$—$NR^{10}$—;

$R^2$ and $R^3$ are independently selected from: H; unsubstituted or substituted $C_{1-8}$ alkyl, unsubstituted or substituted $C_{2-8}$ alkenyl, unsubstituted or substituted $C_{2-8}$ alkynyl, unsubstituted or substituted aryl,

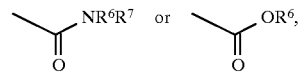

wherein the substituted group is substituted with one or more of:
 1) aryl, unsubstituted or substituted with:
  a) $C_{1-4}$ alkyl,
  b) $(CH_2)_pOR^6$,
  c) $(CH_2)_pNR^6R^7$,
  d) halogen,
  e) CN,
  f) aryl,
  g) perfluoro-$C_{1-4}$ alkyl,
  h) $SR^{6a}$, $S(O)R^{6a}$, $SO_2R^{6a}$,
 2) $C_{3-6}$ cycloakyl,
 3) $OR^6$,
 4) $SR^{6a}$, $S(O)R^{6a}$, or $SO_2R^{6a}$, 6) 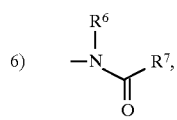

7) 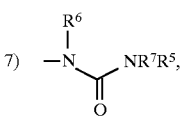

8) —O
    ‖
    C—NR$^6$R$^7$,
    O

9) —O
    ‖
    C—OR$^6$,
    O

10) 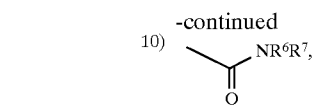

11) —SO$_2$—NR$^6$R$^7$,

12) 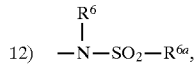

13) 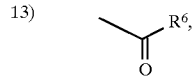

14) 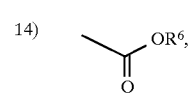

15) N$_3$,
16) F, or
17) perfluoro-C$_{1-4}$-alkyl; or

R$^4$ is selected from H and CH$_3$;
and any two of R$^2$, R$^3$ and R$^4$ are optionally attached to the same carbon atom;

R$^5$, R$^6$ and R$^7$ are independently selected from: H; C$_{1-4}$ alkyl, C$_{3-6}$ cycloalkyl, aryl, aroyl, arylsulfonyl, unsubstituted or substituted with:
a) C$_{1-4}$ alkoxy,
b) aryl,
c) halogen,
d) HO,
e) 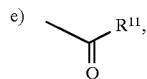
f) —SO$_2$R$^{11}$, or
g) N(R$^{10}$)$_2$; or R$^{6a}$ is selected from: C$_{1-4}$ alkyl, C$_{3-6}$ cycloalkyl, aryl, unsubstituted or substituted with:
a) C$_{1-4}$ alkoxy,
b) aryl,
c) halogen,
d) HO,
e) 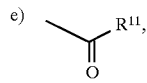
f) —SO$_2$R$^{11}$, or
g) N(R$^{10}$)$_2$;

R$^8$ is independently selected from:
a) hydrogen,
b) aryl, C$_3$–C$_{10}$ cycloalkyl, C$_2$–C$_6$ alkenyl, C$_2$–C$_6$ alkynyl, perfluoroalkyl, F, Cl, Br, R$^{10}$O—, R$^{11}$S(O)$_m$—, R$^{10}$C(O)NR$^{10}$—, (R$^{10}$)$_2$NC(O)—, R$^{10}$$_2$N—C(NR$^{10}$)—, CN, NO$_2$, R$^{10}$C(O)—, N$_3$, —N(R$^{10}$)$_2$, or R$^{11}$OC(O)NR$^{10}$—, and
c) C$_1$–C$_6$ alkyl unsubstituted or substituted by aryl, cyanophenyl, C$_3$–C$_{10}$ cycloalkyl, C$_2$–C$_6$ alkenyl, C$_2$–C$_6$ alkynyl, perfluoroalkyl, F, Cl, Br, R$^{10}$O—, R$^{11}$S(O)$_m$—, R$^{10}$C(O)NH—, (R$^{10}$)$_2$NC(O)—, R$^{10}$$_2$N—C(NR$^{10}$)—, CN, R$^{10}$C(O)—, N$_3$, —N(R$^{10}$)$_2$, or R$^{10}$OC(O)NH—;

R$^9$ is selected from:
a) hydrogen,
b) alkenyl, alkynyl, perfluoroalkyl, F, Cl, Br, R$^{10}$O—, R$^{11}$S(O)$_m$—, R$^{10}$C(O)NR$^{10}$—, (R$^{10}$)$_2$NC(O)—, R$^{10}$$_2$N—C(NR$^{10}$)—, CN, NO$_2$, R$^{10}$C(O)—, N$_3$, —N(R$^{10}$)$_2$, or R$^{11}$OC(O)NR$^{10}$—, and
c) C$_1$–C$_6$ alkyl unsubstituted or substituted by perfluoroalkyl, F, Cl, Br, R$^{10}$O—, R$^{11}$S(O)$_m$—, R$^{10}$C(O)NR$^{10}$—, (R$^{10}$)$_2$NC(O)—, R$^{10}$$_2$N—C(NR$^{10}$)—, CN, R$^{10}$C(O)—, N$_3$, —N(R$^{10}$)$_2$, or R$^{11}$OC(O)NR$^{10}$—;

R$^{10}$ is independently selected from hydrogen, C$_1$–C$_6$ alkyl, benzyl and aryl;

R$^{11}$ is independently selected from C$_1$–C$_6$ alkyl and aryl;

A$^1$ and A$^2$ are independently selected from: a bond, —CH=CH—, —C≡C—, —C(O)—, —C(O)NR$^{10}$—, —NR$^{10}$C(O)—, O, —N(R$^{10}$)—, —S(O)$_2$N(R$^{10}$)—, —N(R$^{10}$)S(O)$_2$—, or S(O)$_m$;

V is selected from:
a) hydrogen,
b) aryl,
c) C$_1$–C$_{20}$ alkyl wherein from 0 to 4 carbon atoms are replaced with a a heteroatom selected from O, S, and N, and
d) C$_2$–C$_{20}$ alkenyl,
provided that V is not hydrogen if A$^1$ is S(O)$_m$ and V is not hydrogen if A$^1$ is a bond, n is 0 and A$^2$ is S(O)$_m$;

W is selected from pyridinyl and imidazolyl;

X is a bond, —CH$_2$—, —C(=O)—, or —S(=O)$_m$—;

Z is selected from:
1) a unsubstituted or substituted group selected from aryl, arylmethyl, arylsulfonyl, wherein the substituted group is substituted with one or more of the following:
a) C$_{1-4}$ alkyl, unsubstituted or substituted with:
C$_{1-4}$ alkoxy, NR$^6$R$^7$, C$_{3-6}$ cycloalkyl, unsubstituted or substituted aryl, HO, —S(O)$_m$R$^{6a}$, or —C(O)NR$^6$R$^7$,
b) aryl,
c) halogen,
d) OR$^6$,
e) NR$^6$R$^7$,
f) CN,
g) NO$_2$,
h) CF$_3$,
i) —S(O)$_m$R$^{6a}$,
j) —C(O)NR$^6$R$^7$, or
k) C$_3$–C$_6$ cycloalkyl; or
2) unsubstituted C$_1$–C$_6$ alkyl, substituted C$_1$–C$_6$ alkyl, unsubstituted C$_3$–C$_6$ cycloalkyl or substituted C$_3$–C$_6$ cycloalkyl,wherein the substituted C$_1$–C$_6$ alkyl and substituted C$_3$–C$_6$ cycloalkyl is substituted with one or two of the following:
a) C$_{1-4}$ alkoxy,
b) NR$^6$R$^7$,
c) C$_{3-6}$ cycloalkyl,
d) —NR$^6$C(O)R$^7$,
e) HO,
f) —S(O)$_m$R$^{6a}$,
g) halogen, or
h) perfluoroalkyl;

m is 0, 1 or 2;
n is 0, 1, 2, 3 or 4;
p is 0, 1, 2, 3 or 4;
q is 1 or 2;
r is 0 to 5, provided that r is 0 when V is hydrogen;

s is 0; and t is 1;

provided that when X is —C(=O)—, or —S(=O)$_m$—, then t is 1 and the substituent (R$^8$)$_r$— V—A$^1$(CR$^{1a}{}_2$)$_n$A$^2$(CR$^{1a}{}_2$)$_n$— is not H;

or a pharmaceutically acceptable salt thereof.

2. The compound according to claim 1 of the formula A:

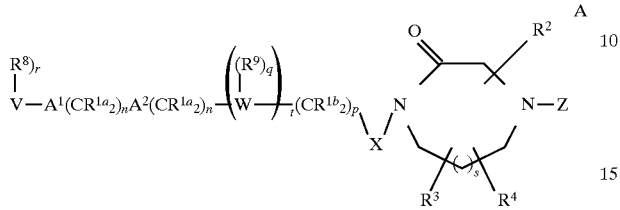

wherein:

R$^{1a}$ is independently selected from: hydrogen or C$_1$–C$_6$ alkyl;

R$^{1b}$ is independently selected from:
 a) hydrogen,
 b) aryl, cycloalkyl, R$^{10}$O—, —N(R$^{10}$)$_2$ or C$_2$–C$_6$ alkenyl,
 c) unsubstituted or substituted C$_1$–C$_6$ alkyl wherein the substitutent on the substituted C$_1$–C$_6$ alkyl is selected from unsubstituted or substituted aryl, cycloalkyl, alkenyl, R$^{10}$O— and —N(R$^{10}$)$_2$;

R$^3$ and R$^4$ are independently selected from H and CH$_3$;

R$^2$ is H;

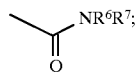

or C$_{1-5}$ alkyl, unbranched or branched, unsubstituted or substituted with one or more of:
 1) aryl,
 2) OR$^6$,
 3) SR$^{6a}$, SO$_2$R$^{6a}$, or 4) 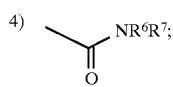

and any two of R$^2$, R$^3$, R$^4$, and R$^5$ are optionally attached to the same carbon atom;

R$^6$ and R$^7$ are independently selected from:
 H; C$_{1-4}$ alkyl, C$_{3-6}$ cycloalkyl, aryl, unsubstituted or substituted with:
  a) C$_{1-4}$ alkoxy,
  b) halogen, or
  c) aryl;

R$^{6a}$ is selected from:
 C$_{1-4}$ alkyl or C$_{3-6}$ cycloalkyl, unsubstituted or substituted with:
  a) C$_{1-4}$ alkoxy,
  b) halogen, or
  c) aryl;

R$^8$ is independently selected from:
 a) hydrogen,
 b) C$_1$–C$_6$ alkyl, C$_2$–C$_6$ alkenyl, C$_2$–C$_6$ alkynyl, C$_1$–C$_6$ perfluoroalkyl, F, Cl, R$^{10}$O—, R$^{10}$C(O)NR$^{10}$—, CN, N$_2$, (R$^{10}$)$_2$N—C(NR$^{10}$)—, R$^{10}$C(O)—, —N(R$^{10}$)$_2$, or R$^{11}$OC(O)NR$^{10}$—, and
 c) C$_1$–C$_6$ alkyl substituted by C$_1$–C$_6$ perfluoroalkyl, R$^{10}$O—, R$^{10}$C(O)NR$^{10}$—, (R$^{10}$)$_2$N—C(NR$^{10}$)—, R$^{10}$C(O)—, —N(R$^{10}$)$_2$, or R$^{11}$OC(O)NR$^{10}$—;

R$^9$ is selected from:
 a) hydrogen,
 b) C$_2$–C$_6$ alkenyl, C$_2$–C$_6$ alkynyl, C$_1$–C$_6$ perfluoroalkyl, F, Cl, R$^{10}$O—, R$^{11}$S(O)$_m$—, R$^{10}$C(O)NR$^{10}$—, CN, NO$_2$, (R$^{10}$)$_2$N—C(NR$^{10}$)—, R$^{10}$C(O)—, —N(R$^{10}$)$_2$, or R$^{11}$OC(O)NR$^{10}$—, and
 c) C$_1$–C$_6$ alkyl unsubstituted or substituted by C$_1$–C$_6$ perfluoroalkyl, F, Cl, R$^{10}$O—, R$^{11}$S(O)$_m$—, R$^{10}$C(O)NR$^{10}$—, CN, (R$^{10}$)$_2$N—C(NR$^{10}$)—, R$^{10}$C(O)—, —N(R$^{10}$)$_2$, or R$^{11}$OC(O)NR$^{10}$—;

R$^{10}$ is independently selected from hydrogen, C$_1$–C$_6$ alkyl, benzyl and

R$^{11}$ is independently selected from C$_1$–C$_6$ alkyl and aryl;

A$^1$ and A$^2$ are independently selected from: a bond, —CH=CH—, —C≡C—, —C(O)—, —C(O)NR$^{10}$—, O, —N(R$^{10}$)—, or S(O)$_m$;

V is selected from:
 a) hydrogen,
 b) aryl,
 c) C$_1$–C$_{20}$ alkyl wherein from 0 to 4 carbon atoms are replaced with a heteroatom selected from O, S, and N, and
 d) C$_2$–C$_{20}$ alkenyl, and provided that V is not hydrogen if A$^1$ is S(O)$_m$ and V is not hydrogen if A$^1$ is a bond, n is 0 and A$^2$ is S(O)$_m$;

W is a heterocycle selected from imidazolyl and pyridinyl;

X is —CH$_2$— or —C(=O)+;

Z is selected from:
 1) a unsubstituted or substituted group selected from aryl, arylmethyl, arylsulfonyl, wherein the substituted group is substituted with one or more of the following:
  a) C$_{1-4}$ alkyl, unsubstituted or substituted with:
   C$_{1-4}$ alkoxy, NR$^6$R$^7$, C$_{3-6}$ cycloalkyl, unsubstituted or substituted aryl, HO, —S(O)$_m$R$^{6a}$, or —C(O)NR$^6$R$^7$,
  b) aryl,
  c) halogen,
  d) OR$^6$,
  e) NR$^6$R$^7$,
  f) CN,
  g) NO$_2$,
  h) CF$_3$;
  i) —S(O)$_m$R$^{6a}$,
  j) —C(O)NR$^6$R$^7$, or
  k) C$_3$–C$_6$ cycloalkyl; or
 2) unsubstituted C$_1$–C$_6$ alkyl, substituted C$_1$–C$_6$ alkyl, unsubstituted C$_3$–C$_6$ cycloalkyl or substituted C$_3$–C$_6$ cycloalkyl, wherein the substituted C$_1$–C$_6$ alkyl and substituted C$_3$–C$_6$ cycloalkyl is substituted with one or two of the following:
  a) C$_{1-4}$ alkoxy,
  b) NR$^6$R$^7$,
  c) C$_{3-6}$ cycloalkyl,
  d) —NR$^6$C(O)R$^7$,
  e) HO,
  f) —S(O)$_m$R$^{6a}$,
  g) halogen, or
  h) perfluoroalkyl;

m is 0, 1 or 2;

n is 0, 1, 2, 3 or 4;

p is 0, 1, 2, 3 or 4;

r is 0 to 5, provided that r is 0 when V is hydrogen;

s is 0; and t is 1;

provided that when X is —C(=O)—, then t is 1 and the substitutent $(R^8)_r$—V—$A^1(CR^{1a}_2)_n A^2(CR^{1a}_2)_n$— is not H;

or a pharmaceutically acceptable salt thereof.

3. The compound according to claim 1 of the formula C:

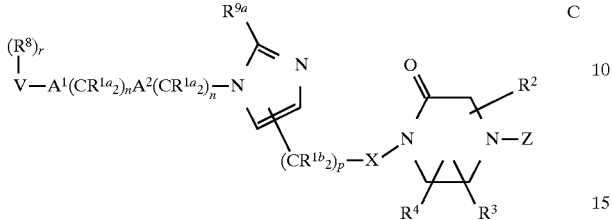

wherein:

$R^{1a}$ is selected from: hydrogen or $C_1$–$C_6$ alkyl;

$R^{1b}$ is independently selected from:
a) hydrogen,
b) aryl, cycloalkyl, $R^{10}O$—, —$N(R^{10})_2$ or $C_2$–$C_6$ alkenyl,
c) $C_1$–$C_6$ alkyl unsubstituted or substituted by aryl, cycloalkyl, alkenyl, $R^{10}O$—, or —$N(R^{10})_2$;

$R^3$ is selected from H and $CH_3$; $R^2$ is selected from H;

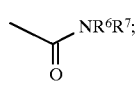

or $C_{1-5}$ alkyl, unbranched or branched,
unsubstituted or substituted with one or more of:
1) aryl,
2) $OR^6$,
3) $SR^{6a}$, $SO_2R^{6a}$, or 4) 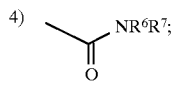

and $R^2$ and $R^3$ are optionally attached to the same carbon atom;

$R^6$ and $R^7$ are independently selected from:
H; $C_{1-4}$ alkyl, $C_{3-6}$ cycloalkyl, aryl, unsubstituted or substituted with:
a) $C_{1-4}$ alkoxy,
b) halogen, or
c) aryl;

$R^{6a}$ is selected from:
$C_{1-4}$ alkyl or $C_{3-6}$ cycloalkyl, unsubstituted or substituted with:
a) $C_{1-4}$ alkoxy,
b) halogen, or
c) aryl;

$R^8$ is independently selected from:
a) hydrogen,
b) $C_1$–$C_6$ alkyl, $C_2$–$C_6$ alkenyl, $C_2$–$C_6$ alkynyl, $C_1$–$C_6$ perfluoroalkyl, F, Cl, $R^{10}O$—, $R^{10}C(O)NR^{10}$—, CN, $N_2$, $(R^{10})_2N$—$C(NR^{10})$—, $R^{10}C(O)$—, —$N(R^{10})_2$, or $R^{11}OC(O)NR^{10}$—, and
c) $C_1$–$C_6$ alkyl substituted by $C_1$–$C_6$ perfluoroalkyl, $R^{10}O$—, $R^{10}C(O)NR^{10}$—, $(R^{10})_2N$—$C(NR^{10})$—, $R^{10}C(O)$—, —$N(R^{10})_2$, or $R^{11}OC(O)NR^{10}$—;

$R^{9a}$ is hydrogen or methyl;

$R^{10}$ is independently selected from hydrogen, $C_1$–$C_6$ alkyl, benzyl and aryl;

$R^{11}$ is independently selected from $C_1$–$C_6$ alkyl and aryl;

$A^1$ and $A^2$ are independently selected from: a bond, —CH=CH—, —C≡C—, —C(O)—, —$C(O)NR^{10}$—, O, —$N(R^{10})$—, or $S(O)_m$;

V is selected from:
a) hydrogen,
b) aryl,
c) $C_1$–$C_{20}$ alkyl wherein from 0 to 4 carbon atoms are replaced with a heteroatom selected from O, S, and N, and
d) $C_2$–$C_{20}$ alkenyl, and provided that V is not hydrogen if $A^1$ is $S(O)_m$ and V is not hydrogen if $A^1$ is a bond, n is 0 and $A^2$ is $S(O)_m$;

X is —$CH_2$— or —C(=O)—;

Z is selected from:
1) a unsubstituted or substituted group selected from aryl, arylmethyl, arylsulfonyl, wherein the substituted group is substituted with one or more of the following:
a) $C_{1-4}$ alkyl, unsubstituted or substituted with:
$C_{1-4}$ alkoxy, $NR^6R^7$, $C_{3-6}$ cycloalkyl, unsubstituted or substituted aryl, HO, —$S(O)_m R^{6a}$, or —$C(O)NR^6R^7$,
b) aryl,
c) halogen,
d) $OR^6$,
e) $NR^6R^7$,
f) CN,
g) $NO_2$,
h) $CF_3$;
i) —$S(O)_m R^{6a}$,
j) —$C(O)NR^6R^7$, or
k) $C_3$–$C_6$ cycloalkyl; or
2) unsubstituted $C_1$–$C_6$ alkyl, substituted $C_1$–$C_6$ alkyl, unsubstituted $C_3$–$C_6$ cycloalkyl or substituted $C_3$–$C_6$ cycloalkyl, wherein the substituted $C_1$–$C_6$ alkyl and substituted $C_3$–$C_6$ cycloalkyl is substituted with one or two of the following:
a) $C_{1-4}$ alkoxy,
b) $NR^6R^7$,
c) $C_{3-6}$ cycloalkyl,
d) —$NR^6C(O)R^7$,
e) HO,
f) —$S(O)_m R^{6a}$,
g) halogen, or
h) perfluoroalkyl;

m is 0, 1 or 2;

n is 0, 1, 2, 3 or 4;

p is 0, 1, 2, 3 or 4; and r is 0 to 5, provided that r is 0 when V is hydrogen; provided that when X is —C(=O)—, then the substitutent $(R^8)_r$— V—$A^1(CR^{1a}_2)_n A^2(CR^{1a}_2)_n$— is not H;

or an optical isomer or pharmaceutically acceptable salt thereof.

4. The compound according to claim 3 of the formula D:

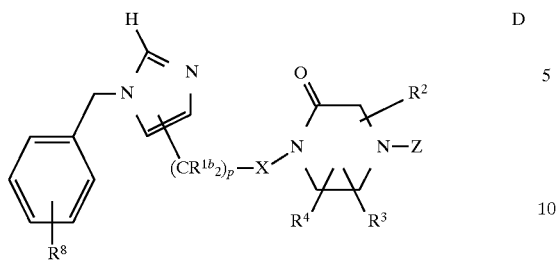

wherein:
R$^{1b}$ is independently selected from:
  a) hydrogen,
  b) aryl, cycloalkyl, R$^{10}$O—, —N(R$^{10}$)$_2$ or C$_2$–C$_6$ alkenyl,
  c) C$_1$–C$_6$ alkyl unsubstituted or substituted by aryl, cycloalkyl, alkenyl, R$^{10}$O—, or —N(R$^{10}$)$_2$;
R$^3$ is selected from H and CH$_3$;

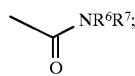

R$^2$ is selected from H;
or C$_{1-5}$ alkyl, unbranched or branched, unsubstituted or substituted with one or more of:
  1) aryl,
  2) OR$^6$,
  3) SR$^{6a}$, SO$_2$R$^{6a}$, or
  4) ![NR6R7 group]

and R$^2$ and R$^3$ are optionally attached to the same carbon atom;
R$^6$ and R$^7$ are independently selected from:
  H; C$_{1-4}$ alkyl, C$_{3-6}$ cycloalkyl, aryl, unsubstituted or substituted with:
    a) C$_{1-4}$ alkoxy,
    b) halogen, or
    c) aryl;
R$^{6a}$ is selected from:
  C$_{1-4}$ alkyl or C$_{3-6}$ cycloalkyl, unsubstituted or substituted with:
    a) C$_{1-4}$ alkoxy,
    b) halogen, or
    c) aryl;
R$^8$ is independently selected from:
  a) hydrogen,
  b) C$_1$–C$_6$ alkyl, C$_2$–C$_6$ alkenyl, C$_2$–C$_6$ alkynyl, C$_1$–C$_6$ perfluoroalkyl, F, Cl, R$^{10}$O—, R$^{10}$C(O)NR$^{10}$—, CN, N$_2$, (R$^{10}$)$_2$N—C(NR$^{10}$)—, R$^{10}$C(O)—, R$^{10}$OC(O)—, —N(R$^{10}$)$_2$, or R$^{11}$OC(O)NR$^{10}$—, and
  c) C$_1$–C$_6$ alkyl substituted by C$_1$–C$_6$ perfluoroalkyl, R$^{10}$O—, R$^{10}$C(O)NR$^{10}$—, (R$^{10}$)$_2$N-C(NR$^{10}$)—, R$^{10}$C(O)—, R$^{10}$OC(O)—, —N(R$^{10}$)$_2$, or R$^{11}$OC(O)NR$^{10}$—;
R$^{10}$ is independently selected from hydrogen, C$_1$–C$_6$ alkyl, benzyl and aryl;
R$^{11}$ is independently selected from C$_1$–C$_6$ alkyl and aryl;
X is —CH$_2$— or —C(=O)—;

Z is selected from:
  1) a unsubstituted or substituted group selected from aryl, arylmethyl, arylsulfonyl, wherein the substituted group is substituted with one or more of the following:
    a) C$_{1-4}$ alkyl, unsubstituted or substituted with:
      C$_{1-4}$ alkoxy, NR$^6$R$^7$, C$_{3-6}$ cycloalkyl, unsubstituted or substituted aryl, HO, —S(O)$_m$R$^{6a}$, or —C(O)NR$^6$R$^7$,
    b) aryl,
    c) halogen,
    d) OR$^6$,
    e) NR$^6$R$^7$,
    f) CN,
    g) NO$_2$,
    h) CF$_3$;
    i) —S(O)$_m$R$^{6a}$,
    j) —C(O)NR$^6$R$^7$, or
    k) C$_3$–C$_6$ cycloalkyl; or
  2) unsubstituted C$_1$–C$_6$ alkyl, substituted C$_1$–C$_6$ alkyl, unsubstituted C$_3$–C$_6$ cycloalkyl or substituted C$_3$–C$_6$ cycloalkyl, wherein the substituted C$_1$–C$_6$ alkyl and substituted C$_3$–C$_6$ cycloalkyl is substituted with one or two of the following:
    a) C$_{1-4}$ alkoxy,
    b) NR$^6$R$^7$,
    c) C$_{3-6}$ cycloalkyl,
    d) —NR$^6$C(O)R$^7$,
    e) HO,
    f) —S(O)$_m$R$^{6a}$,
    g) halogen, or
    h) perfluoroalkyl;
m is 0, 1 or 2; and
p is 0, 1, 2, 3 or 4;
or pharmaceutically acceptable salt thereof.

5. A compound which inhibits famesyl-protein transferase which is:
  4-(3-Chlorophenyl)-1-[1-(4-cyanobenzyl)-5-imidazolylmethyl]-2-piperazinone
  (S)-6-n-Butyl-1-[1-(4-cyanobenzyl)-5-imidazolylmethyl]-4-(2,3-dimethylphenyl)-2-piperazinone and
  4-(3-Chlorophenyl)-1-[(3-(4-cyanobenzyl)pyridin-4-yl)methyl]-2-piperazinone
or a pharmaceutically acceptable salt or optical isomer thereof.

6. A compound which inhibits famesyl-protein transferase which is:
  4-(3-Chlorophenyl)-1-[1-(4-cyanobenzyl)-5-imidazolylmethyl]-2-piperazinone

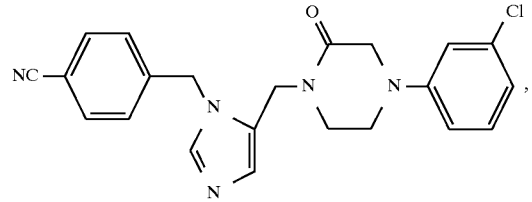

or a pharmaceutically acceptable salt or optical isomer thereof.

7. A pharmaceutical composition comprising a pharmaceutical carrier, and dispersed therein, a therapeutically effective amount of a compound of claim 1.

8. A pharmaceutical composition comprising a pharmaceutical carrier, and dispersed therein, a therapeutically effective amount of a compound of claim 2.

9. A pharmaceutical composition comprising a pharmaceutical carrier, and dispersed therein, a therapeutically effective amount of a compound of claim 5.

10. A method for inhibiting farnesyl-protein transferase which comprises administering to a mammal in need thereof a therapeutically effective amount of a composition of claim 7.

11. A method for inhibiting farnesyl-protein transferase which comprises administering to a mammal in need thereof a therapeutically effective amount of a composition of claim 8.

12. A method for inhibiting farnesyl-protein transferase which comprises administering to a mammal in need thereof a therapeutically effective amount of a composition of claim 9.

* * * * *

UNITED STATES PATENT AND TRADEMARK OFFICE
CERTIFICATE OF CORRECTION

PATENT NO. : 5,885,995
DATED : March 23, 1999
INVENTOR(S) : Christopher J. Dinsmore It is certified that error appears in the above-identified patent and that said Letters Patent is hereby corrected as shown below:

On the title page: Item [60] Related U.S. Application Data: should read:

--Provisional application No. 60/014,792 Apr. 3, 1996--.

Signed and Sealed this

Fourteenth Day of September, 1999

Attest:

Q. TODD DICKINSON

*Attesting Officer*    *Acting Commissioner of Patents and Trademarks*